United States Patent
Marks et al.

(10) Patent No.: US 9,388,244 B2
(45) Date of Patent: *Jul. 12, 2016

(54) INTERNALIZING ERBB2 ANTIBODIES

(71) Applicant: The Regents of the University of California, Oakland, CA (US)

(72) Inventors: James D. D. Marks, Kensington, CA (US); Marie Alix Poul, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/627,773

(22) Filed: Feb. 20, 2015

(65) Prior Publication Data

US 2015/0239976 A1 Aug. 27, 2015

Related U.S. Application Data

(60) Continuation of application No. 13/441,651, filed on Apr. 6, 2012, now Pat. No. 8,974,792, which is a division of application No. 12/928,792, filed on Dec. 16, 2010, now Pat. No. 8,173,424, which is a division of application No. 11/809,773, filed on Jun. 1, 2007, now Pat. No. 7,892,554, which is a division of application No. 09/250,056, filed on Feb. 12, 1999, now Pat. No. 7,244,826.

(60) Provisional application No. 60/082,953, filed on Apr. 24, 1998.

(51) Int. Cl.

| | |
|---|---|
| A61K 39/395 | (2006.01) |
| C07K 16/18 | (2006.01) |
| C07K 16/28 | (2006.01) |
| C07K 16/30 | (2006.01) |
| C07K 17/06 | (2006.01) |
| C07K 17/08 | (2006.01) |
| A61K 47/48 | (2006.01) |
| C07K 16/32 | (2006.01) |
| C12N 15/86 | (2006.01) |
| A61K 31/704 | (2006.01) |
| A61K 9/00 | (2006.01) |
| A61K 38/00 | (2006.01) |

(52) U.S. Cl.
CPC ........... *C07K 16/2863* (2013.01); *A61K 9/0019* (2013.01); *A61K 31/704* (2013.01); *A61K 47/48538* (2013.01); *A61K 47/48569* (2013.01); *A61K 47/48584* (2013.01); *A61K 47/48623* (2013.01); *A61K 47/48823* (2013.01); *C07K 16/2881* (2013.01); *C07K 16/30* (2013.01); *C07K 16/3053* (2013.01); *C07K 16/32* (2013.01); *C12N 15/86* (2013.01); *A61K 38/00* (2013.01); *C07K 2317/10* (2013.01); *C07K 2317/21* (2013.01); *C07K 2317/565* (2013.01); *C07K 2317/622* (2013.01); *C07K 2317/626* (2013.01); *C07K 2317/77* (2013.01); *C07K 2317/92* (2013.01); *C07K 2319/02* (2013.01); *C12N 2795/10043* (2013.01); *C12N 2810/859* (2013.01); *Y10S 424/812* (2013.01)

(58) Field of Classification Search
CPC .... C07K 16/28; C07K 16/2863; C07K 16/30; C07K 16/3015; C07K 17/08; A61K 9/1271; A61K 39/395; A61K 39/39533; A61K 39/39558; A61K 47/14; A61K 31/133; A61K 31/135; A61K 31/192; A61K 31/196; A61K 31/235; A61K 31/351; A61K 31/704
See application file for complete search history.

(56) References Cited

U.S. PATENT DOCUMENTS

| | | | |
|---|---|---|---|
| 5,169,774 | A | 12/1992 | Frankel et al. |
| 5,242,824 | A | 9/1993 | Hellstrom et al. |
| 5,696,237 | A | 12/1997 | Fitzgerald et al. |
| 5,733,782 | A | 3/1998 | Dorai et al. |
| 5,885,793 | A | 3/1999 | Griffeths et al. |
| 6,054,312 | A | 4/2000 | Larocca et al. |
| 6,214,388 | B1 | 4/2001 | Benz et al. |
| 7,138,501 | B2 | 11/2006 | Ruben et al. |

FOREIGN PATENT DOCUMENTS

| | | |
|---|---|---|
| WO | WO 91/00996 | 7/1991 |
| WO | WO 92/06176 A1 | 4/1992 |
| WO | WO 92/22653 A | 12/1992 |
| WO | WO 94/05781 A1 | 3/1994 |
| WO | WO 94/11496 A1 | 5/1994 |
| WO | WO 94/13804 A | 6/1994 |
| WO | WO 94/26787 A1 | 11/1994 |
| WO | WO 96/21007 A | 7/1996 |
| WO | WO 97/00271 A | 1/1997 |

(Continued)

OTHER PUBLICATIONS

U.S. Appl. No. 13/441,651, filed Apr. 6, 2012 by James D. Marks, et al.
U.S. Appl. No. 12/928,792, filed Dec. 16, 2010 by James D. Marks, et al.
U.S. Appl. No. 11/777,989, filed Jul. 13, 2007 by James D. Marks, et al.
U.S. Appl. No. 11/809,773, filed Jun. 1, 2007 by James D. Marks, et al.
U.S. Appl. No. 09/250,056, filed Feb. 12, 1999 by James D. Marks, et al.
Adams et al. (1993) "Highly Specific in Vivo Tumor Targeting by Monovalent and Divalent Forms of 741F8 Anti-c-erbB-2 Singla Chain Fv." *Cancer Research*, 53(17): 4026-4034.

(Continued)

*Primary Examiner* — Alana Harris Dent
*Assistant Examiner* — Anne Holleran
(74) *Attorney, Agent, or Firm* — Quine Intellectual Property Law Group, P.C.

(57) ABSTRACT

This invention provides novel erbB2-binding internalizing antibodies. The antibodies, designated F5 and C1, specifically bind to c-erbB2 antigen and, upon binding, are readily internalized into the cell bearing the c-erbB2 marker. Chimeric molecules comprising the F5 and/or C1 antibodies attached to one or more effector molecules are also provided.

21 Claims, 2 Drawing Sheets

(56) References Cited

FOREIGN PATENT DOCUMENTS

| WO | WO 97/10330 A | 3/1997 |
|---|---|---|
| WO | WO 97/38723 A | 10/1997 |
| WO | WO 97/45544 A | 12/1997 |
| WO | WO 98/05344 A | 2/1998 |
| WO | WO 99/10014 A | 3/1999 |

OTHER PUBLICATIONS

Adams et al. (1998) "Increased Affinity Leads to Improved Selective Tumor Delivery of Single-Chain Fv Antibodies." *Cancer Research* 58(3): 485-490.
Allred et al. (1992) "Overexpression of HER-2/neu and its Relationship with other prognostic factors change during the progression of in situ to invasive breat cancer." *Human Pathology*, 23(9): 974-979.
Altenschmidt et al. (1997) "Targeted Therapy of Schwannoma Cells in Immunocompetent Rats with an erbB2-Specific Antibody-Toxin." *International Journal of Cancer*, 73(1): 117-124.
Amit et al. (1986) Science, 233:747-753.
Andersen et al. (1996) "A recombinant antibody with the antigen-specific, major histocompatibility complex-restricted specificity of T cells," *Proceedings of the National Academy of Sciences* 93(5): 1820-1824.
Barry et al. (1996) "Toward cell-targeting gene therapy vectors: Selection of cell-binding peptides from random peptide-presenting phage libraries." *Nature*, 2(3): 299-305.
Barton et al., Protein Structural Prediction, A practical approach, pp. 31-63, (1996).
Bird et al. (1988) Science, 242:4423-4426.
Borrebaeck (1989) "Strategy for the production of human monoclonal antibodies using in vitro activated B cells." *Journal of Immunological Methods*, 123: 157-165.
Brinkmann et al. (1993) "A recombinant immunotoxin that is active on prostate cancer cells and that is composed on the Fv region of molocIona; antibody PR1 and a truncated form of Pseudomonas exotoxin." *Proceedings of the National Academy of Sciences, USA*, 90: 547-551.
Cai et al. (1995) "Anti-melanoma antibodies from melanoma patients immunized with genetically modified autologous tumor cells: Selection of specific antibodies from single-chain Fv fusion phage libraries." *Proceedings of the National Academy of Sciences* 92(14): 6537-6541.
Carter et al. (1994) "Towards an immunotherapy for p185HER2 over expression tumors." *Antigen & Antibody Engineering in Breast Cancer Diagnosis*, pp. 83-94.
Casalini et al. (1993) "A critical comparison of three internalization assays applied to the evaluation of a given mAb as a toxin-carrier candidate." *Cancer Immunology Immunotherapy*, 37: 54-60.
Casset et al. (2003) *BBRC*, 307: 198-205.
Chan et al. (1999) *Journal of Molecular Biology*, 293: 865-881.
Chaudhary et al. (1990) PNAS, 87:1066-1070.
Clackson et al (1991) "Making antibody fragments using phage display libraries." *Nature*, 352: 624-628.
Colcher et al. (1988) "Radioimmunolocalization of Human Carcinoma Xenographs with B72.3 Second Generation Monoclonal Antibodies." *Cancer Research*, 48: 4597-4603.
De Kruif et al. (1995) "Rapid selection of cell subpopulation-specific human monoclonal antibodies from a synthetic phage antibody library." *Proceedings of the National Academy of Sciences* 92(6): 3938-3942.
De Kruif et al. (1995) "Selection and Application of Human Single Chain Fv Antibody Fragments from a Semi-synthetic Phage Antibody Display Library with Designed CDR3 Regions." *Journal of Molecular Biology* 248(1): 97-105.
De Pascallis et al. (2002) *The Journal of Immunology*, 169: 3076-3084.
Disis et al. (1994) "Existent T-Cell and Antibody Immunity to HER-2/neu Protein in Patients with Breast Cancer." *Cancer Research*, 54: 16-20.

Douglas et al. (1996) "Targeted gene delivery by tropism-modified adenoviral vectors." *Nature Biotechnology* 14:1574-1578.
Fominaya et al. (1996) "Target Cell-Specific DNA Transfer Mediated by a Chimeric Multidomain Protein." *Journal of Biological Chemistry*, 271(18): 10560-10568.
Gallinger et al. (1993) "Comparative Dual Label Study of First and Second Generation Antiumor-associated Glycoprotein-72 Monoclonal Antibodies in Colorectal Cancer Patients." *Cancer Research*, 53: 273-278.
George et al. (1988) Macromolecular Sequencing and Synthesis, p. 127-149.
Greenspan et al. (1999) Nature Biotechnology, vol. 17, pp. 936-937.
Griffiths et al. (1993) "Human anti-self antibodies with high specificity from phage display libraries." *EMBO Journal*, 12(2): 725-734.
Griffiths et al. (1994) "Isolation of high affinity human antibodies directly from large synthetic repertories." *The EMBO Journal* 13(14): 3245-3260.
Group, E.B.C.T.C. (1992) "Systemic Treatment of Early Breast Cancer by Hormonal Cytotoxic, or immune therapy." *Lancet*, 339: 1-15.
Hart et al. (1994) "Cell Binding and Internalization by Filamentous Phage Displaying Cyclic Arg-Gly-Asp-containing Peptide." *Journal of Biological Chemistry*, 269(17): 12468-12474.
Hawkins et al. (1992) "Selection of Phage Antibodies by Binding Affinity Mimicking Affinity Maturation." *Journal of Nolecular Bilogy*, 226: 889-896.
Holm et al. (2007) *Mollecular Immunology*, 44 : 1075-1108.
Holt et al. (2003) "Domain antibodies: proteins for therapy." *Trends in Biotechnology* 21(11): 484-490.
Hoogenboom et al. (1992) "Building Antibodies from their Genes." *Immunological Reviews*, 130: 41-68.
Hoogenboom et al. (1998) "Antibody phage display technology and its applications." *Immunology* 4(1): 1-20.
Hudziak et al. (1989) "p185$^{HER2}$ Monoclonal Antibody has Antiproliferative Effects in vitro and Sensitizes Human Breast Tumor Cells to Tumor Necrosis Factor." *Molecular and Cellular Biology* 9(3): 1165-1172.
Hurwitz et al. (1995) "Suppression and promotion of tumor growth by monoclonal antibodies to ErbB-2 differentially correlate with cellular uptake." *Proceedings of the National Academy of Sciences USA* 92(8): 3353-3357.
Huston et al. (1988) "Protein engineering of antibody binding sites: Recovery of specific activity in an anti-digoxin single-chain Fv analogue produced in *Escherichia coli*." *Proceedings of the National Academy of Sciences, USA*, 85: 5879-5883.
Ishida et al. (1994) Jpn. J. Cancer Res. 85:172-178.
Kasahara et al. (1994) "Tissue-Specific Targeting of Retroviral Vectors Through Ligand-Receptors Interactions." *Science* 266: 1373-1376.
Kirpotin et al. (1997) "Sterically Stabilized Anti-HER2 Immunoliposomes: Design and Targeting to Human Breast Cancer Cells in Vitro." *Biochemistry*, 36(1): 66-75.
Knight (1989) Bio. Technology, vol. 7, No. 1.
Larocca et al. (1989) "Targeting Becteriophage to Mammalian Cell Surface Receptor for Gene Delivery." *Human Gene Therapy*, 9: 2393-2399.
Larocca et al. (1999) "Gene Transfer to Mammalian Cells Using Genetically Filamentous Bacteriophage." *FASEB Journal*, 13(6): 727-734.
Lewis et al. (1993) "Differential responses of human tumor cell lines to anti-p185HER2 monoclonal antibodies." *Cancer, Immunology, Immunotherapy* 37(4): 255-263.
MacCallum et al. (1996) *Journal of Molecular Biology*, 262: 732-745.
Maier et al. (1991) Cancer Res., 51:5361-5369.
Mandler et al. (2000) Journal of the National Cancer Inst., 92:1573-1581.
Marks et al. (1991) "By-passing Immunization Human: Human antibodies from V-gene Libraries Displayed on Phage." *Journal of Molecular Biology*, 222: 581-597.
Marks et al. (1992) "By-passing Immunization Human: Building High Affinity Human Antibodies by Chain Shuffling." *Bio/Technology*, 10: 779-783.

(56) References Cited

OTHER PUBLICATIONS

Marks et al. (1992) "Molecular Evolution of Proteins on Filamentous Phage." *Journal of Biological Chemistry* 267(23): 16007-16010.
Marks et al. (1992) "Moleculsr Evolution of Proteins on Filamentous Phage." *The Journal of Biology Chemistry*, 267(23): 16007-16010.
Marks et al. (1993) "Human Antibody Fragments Specific for Human Blood Group Antigens from a Phage Display Library." *BioTechnology* 11(10): 1145-1149.
Maynard et al. (2000) *Annu. Rev. Biomed. Eng*, 351-353.
McCafferty et al. (1990) "Phage Antibodies: filamentous phage displaying antibody variable domains." *Nature*, 348: 552-554.
Mendelsohn (2001) Journal of the National Cancer Inst., 92:1549-1551.
Michael et al. (1994) "Strategies to achieve targeted gene delivery via the receptor-medicated endocytosis pathway." *Gene Therapy* 1(4): 223-232.
Nissim et al. (1994) "Antibody fragments from a 'single pot' phage display library as immunochemical reagents." *The EMBO Journal* 13(3): 692-698.
Okayama et al. (1985) "Bacteriophage Lambda Vector for Transducing a cDNA Clone Library into Mammalian Cells." *Molecular and Cellular Biology*, 5(5): 1136-1142.
Panka et al. (1988) Proc. Natl. Acad. Sci., USA 85:3080-3084.
Park et al. (2001) Journal of Controlled Release, 74:95-113.
Paul (1993) Fundamental Immunology, 242.
Pereira et al. (1997) "A model system for detection and isolation of a tumor cell surface antigen using antibody phage display." *Journal of Immunological Methods* 203(1): 11-.24.
Reichmann et al (1993) "Phage Display and Selection of a Site-Directed Randomized Single-Chain Antibody Fv Fragment for Its Affinity Improvement." *Biochemistry*, 32: 8848-8855.
Riethmuller et al. (1992) "Monoclonal antibodies in the detection and therapy of micrometastatic epithelial cancers." *Current Opinion in Immunology*, 4: 647-655.
Rudikoff (1979) "Single amino acid substitution altering antigen-binding specificity" *Proceedings of the National Academy of Sciences, USA*, 79: 1979-1983.
Rudikoff et al. (1982) Proc. Natl. Acad. Sci., USA 79, p. 1979.
Salmon et al. (1987) "Human Breast Cancer: Correlation of Relapse and Survival with Amplification of the HER-2/neu Oncogene." *Science*, 235: 177-182.
Salmon et al. (1989) "Studies of the HER-2/nue Proto-oncogene in Human Breast and Ovarian Cancer." *American Association for the Advancement of Science*, 244(4905): 707-712.
Schier et al. (1995) "In vitro and in vivo characterization of a human anti-c-erbB-2 single-chain Fv isolated from a filamentous phage antibody library." *Immunotechnology*, 1: 73-981.
Schier et al. (1996) "Efficient in vitro affinity maturation of phage antibodies using BIAcore guided selections." *Human Antibody Hybridomas*, 3(7): 97-105.
Schier et al. (1996) "Identification of functional and structural amino-acid residues by parsimonious mutagenesis." *Gane*, 169(2): 147-155.
Schier et al. (1996) "Isolation of High-affinity Monomeric Human Anti-c-crB-2 Single chain Fv Using Affinity-driven Selection." *Journal of Molecular Biology*, 255(1): 28-43.
Schier et al. (1996) "Isolation of Picomolar Affinity Anti-c-erbB-2 Single-chain Fv by Molecular Evolution of the Complementarity Determining Regions in the Center of the Antibody Binding Site." *Journal of Molecular Biology*, 263(4): 551-567.
Sheets et al. (1998) "Efficient construction of a large nonimmune phage antibody library." *Proceedings of the National Academy of Sciences* 95(11): 6157-6162.
Shepard et al. (1991) "Monoclonal Antibody Therapy of Human Cancer: Taking the HER2 Protooncogenic to the Clinic." *Journal of Clinical Immunology*, 11(3): 117-127.
Soderlind et al. (1992) "Phage Display Technology in Antibody Engineering: Design of Phagemid Vectors and in vitro Maturation systems." *Immunological Reviews*, 130: 109-124.
Somia et al. (1995) "Generation of targeted retroviral vectors by using single-chain variable fragment: an approach to in vivo gene delivery." *Proceedings of the National Academy of Sciences* 92(16): 7570-7574.
Stancovski et al. (1991) "Mechanistic aspects of the opposing effects of monoclonal antibodies to the ERBB2 receptor on tumor growth." *Proceedings of the National Academy of Sciences* 88(19): 8691-8698.
Stausbøl-Grøn et al. (1996) "A model phage display subtraction method with potential for analysis of differential gene expression." *FEBS Letters* 391: 71-75.
Trail et al. (1993) "Cure of Xenografted Human Carcinomas by BR96-Doxorubicin Immunoconjugates." *Science*, 261: 212-215.
Ullrich et al. (1990) "Signal Transduction by Receptors with Tyrosine Kinase Activity." *Cell* 61(2): 203-212.
Vajdos et al. (2002) *Journal of Molecular Biology*, 320: 415-428.
Vallera (1994)"Immunotoxins: Will Their Clinical Promise be Fulfilled." *Blood: The Journal of the American Society of Hematology*, 83(2): 309-317.
Van Ewijk et al. (1997) "Subtractive isolation of phage-displayed single-chain antibodies to thymic stromal cells by using intact thymic fragments." *Proceedings of the National Academy of Sciences* 94: 3903-3908.
Vaughan et al. (1996) "Human Antibodies with Sub-nanomolar Affinities Isolated from a Large Non-immunized Phage Display Library." *Nature Biotechnology* 14: 309-314.
Watkins et al. (1997) "The 'adenobody' approach to viral targeting: specific and enhanced adenoviral gene delivery." *Gene Therapy* 4(10): 1004-1012.
Watters et al. (1997) "An optimized method for cell-based phage display panning." *Immunotechnology* 3: 21-29.
Weiner et al. (1989) "Phase I Evaluation of an Anti-Breast Carcinoma Monoclonal Antibody 260F9-Recombinant Ricin a Chain Immunoconjugate." *Cancer Research*, 49: 4062-4067.
Winter et al. (1994) "Making Antibodies by Phage Display Technology." *Annual Reciews of Immunology*, 12: 433-455.
Wu et al. (1999) *Journal of Molecular Biology*, 294: 151-162.
Xu (1993) *Int. J. Cancer*, 53: 401-408.
Yarden (1990) "Agonistic antibodies stimulate the kinase encoded by the neu protooncogene in living cells but the oncogenic mutant is constitutively active." *Proceedings of the National Academy of Sciences* 87(7): 2569-2573.
Yokoyama-Kobayashi et al. (1993) "Recombinant fl Phage Particles Can Transfect Monkey COS-7 Cells by DEAE Dextran Method." *Biochemical and Biophysical Research Communication*, 192(2): 935-939.

SEQUENCE LISTING

```
<160> NUMBER OF SEQ ID NOS: 8

<210> SEQ ID NO 1
<211> LENGTH: 246
<212> TYPE: PRT
<213> ORGANISM: Artificial
<220> FEATURE:
<223> OTHER INFORMATION: scFv F5 amino acid sequence
<220> FEATURE:
<221> NAME/KEY: DOMAIN
<222> LOCATION: (31)..(35)
<223> OTHER INFORMATION: VH-CDR1
<220> FEATURE:
<221> NAME/KEY: DOMAIN
<222> LOCATION: (50)..(66)
<223> OTHER INFORMATION: VH-CDR2
<220> FEATURE:
<221> NAME/KEY: DOMAIN
<222> LOCATION: (99)..(108)
<223> OTHER INFORMATION: VH-CDR3
<220> FEATURE:
<221> NAME/KEY: DOMAIN
<222> LOCATION: (157)..(170)
<223> OTHER INFORMATION: VL-CDR1
<220> FEATURE:
<221> NAME/KEY: DOMAIN
<222> LOCATION: (186)..(192)
<223> OTHER INFORMATION: VL-CDR2
<220> FEATURE:
<221> NAME/KEY: DOMAIN
<222> LOCATION: (225)..(235)
<223> OTHER INFORMATION: VL-CDR3

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Thr Ser Asn Ala Phe Ala Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Gly Ala Pro Gly Gln Arg Val Thr Ile Ser Cys Thr Gly Ser Ser
145                 150                 155                 160

Ser Asn Ile Gly Ala Gly Tyr Gly Val His Trp Tyr Gln Gln Leu Pro
                165                 170                 175

Gly Thr Ala Pro Lys Leu Leu Ile Tyr Gly Asn Thr Asn Arg Pro Ser
            180                 185                 190
```

```
Gly Val Pro Asp Arg Phe Ser Gly Phe Lys Ser Gly Thr Ser Ala Ser
            195                 200                 205

Leu Ala Ile Thr Gly Leu Gln Ala Glu Asp Ala Asp Tyr Tyr Cys
    210                 215                 220

Gln Ser Tyr Asp Ser Ser Leu Ser Gly Trp Val Phe Gly Gly Gly Thr
225                 230                 235                 240

Lys Leu Thr Val Leu Gly
                245

<210> SEQ ID NO 2
<211> LENGTH: 242
<212> TYPE: PRT
<213> ORGANISM: Artificial
<220> FEATURE:
<223> OTHER INFORMATION: scFv C1 amino acid sequence
<220> FEATURE:
<221> NAME/KEY: DOMAIN
<222> LOCATION: (31)..(35)
<223> OTHER INFORMATION: VH-CDR1
<220> FEATURE:
<221> NAME/KEY: DOMAIN
<222> LOCATION: (50)..(66)
<223> OTHER INFORMATION: VH-CDR2
<220> FEATURE:
<221> NAME/KEY: DOMAIN
<222> LOCATION: (99)..(108)
<223> OTHER INFORMATION: VH-CDR3
<220> FEATURE:
<221> NAME/KEY: DOMAIN
<222> LOCATION: (157)..(167)
<223> OTHER INFORMATION: VL-CDR1
<220> FEATURE:
<221> NAME/KEY: DOMAIN
<222> LOCATION: (184)..(190)
<223> OTHER INFORMATION: VL-CDR2
<220> FEATURE:
<221> NAME/KEY: DOMAIN
<222> LOCATION: (223)..(231)
<223> OTHER INFORMATION: VL-CDR3

<400> SEQUENCE: 2

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ser Ile Ser Gly Ser Ser Arg Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Asp Ala Ser Gly Ser Tyr Phe Asn Phe Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Glu Thr Thr Leu Thr Gln Ser Pro Ser Phe
    130                 135                 140

Leu Ser Ala Phe Val Gly Asp Arg Ile Thr Ile Thr Cys Arg Ala Ser
145                 150                 155                 160

Pro Gly Ile Arg Asn Tyr Leu Ala Trp Tyr Gln Gln Lys Pro Gly Lys
                165                 170                 175
```

```
Ala Pro Lys Leu Leu Ile Tyr Ala Ala Ser Thr Leu Gln Ser Gly Val
        180                 185                 190

Pro Ser Arg Phe Ser Gly Ser Gly Ser Gly Thr Asp Phe Thr Leu Thr
    195                 200                 205

Ile Ser Ser Leu Gln Pro Glu Asp Phe Ala Thr Tyr Tyr Cys Gln Gln
    210                 215                 220

Tyr Asn Ser Tyr Pro Leu Ser Phe Gly Gly Gly Thr Lys Val Glu Ile
225                 230                 235                 240

Lys Arg

<210> SEQ ID NO 3
<211> LENGTH: 738
<212> TYPE: DNA
<213> ORGANISM: Artificial
<220> FEATURE:
<223> OTHER INFORMATION: nucleic acid encoding  scFv F5 Ab

<400> SEQUENCE: 3
caggtgcagc tggtggagtc tgggggaggc ttggtacagc ctggggggtc cctgagactc      60
tcctgtgcag cctctggatt cacctttcgc agctatgcca tgagctgggt ccgccaggct     120
ccagggaagg gctggagtg gtctcagct attagtggtc gtggtgataa cacatactac      180
gcagactccg tgaagggccg gttcaccatc tccagagaca attccaagaa cacgctgtat     240
ctgcaaatga acagcctgag agccgaggac acggccgttt attactgtgc gaaaatgaca     300
agtaacgcgt tcgcatttga ctactggggc cagggaaccc tggtcaccgt ctcctcaggt     360
ggaggcggtt caggcggagg tggctctggc ggtggcggat cgcagtctgt gttgacgcag     420
ccgccctcag tgtctggggc cccagggcag agggtcacca tctcctgcac tgggagcagc     480
tccaacatcg ggcaggtta tgtgtacac tggtaccagc agcttccagg aacagccccc      540
aaactcctca tctatggtaa caccaatcgg ccctcagggg tccctgaccg attctctggc     600
ttcaagtctg gcacctcagc ctccctggcc atcactgggc tccaggctga ggatgaggct     660
gattattact gccagtccta tgacagcagc ctgagtggtt gggtgttcgg cggagggacc     720
aagctgaccg tgctaggt                                                   738

<210> SEQ ID NO 4
<211> LENGTH: 726
<212> TYPE: DNA
<213> ORGANISM: Artificial
<220> FEATURE:
<223> OTHER INFORMATION: Nucleic acid encoding scFv C1 amino acid
      sequence
<220> FEATURE:
<221> NAME/KEY: misc_feature
<222> LOCATION: (111)..(111)
<223> OTHER INFORMATION: N = A, C, G, or T

<400> SEQUENCE: 4
caggtgcagc tggtggagtc tgggggaggc ttggtacagc ctggggggtc cctgagactc      60
tcctgtgcag cctctggatt cacctttagc agctatgcca tgggctgggt ncgccaggct    120
ccagggaagg gctggagtg gtctcatca attagtggca gtagtagata catatattac     180
gcagactccg tgaagggccg gttcaccatc tcccagaca attccaagaa cacgctgtat     240
ctgcaaatga acagcctgcg agccgaggac acggccgttt attactgtgc gaaaatggat     300
gcttcgggga gttattttaa tttctggggc cagggcaccc tggtcaccgt ctcctcaggt     360
ggaggcggtt caggcggagg tggctctggc ggtggcggat cggaaacgac actcacgcag     420
```

```
tctccatcct tcctgtctgc atttgtagga gacagaatca ccatcacttg ccgggccagt    480
ccgggcatta ggaattattt agcctggtat cagcaaaaac cagggaaagc ccctaagctc    540
ctgatctatg ctgcatctac tttgcaaagt ggggtcccat caaggttcag cggcagtgga    600
tctgggacag attttactct caccatcagc agcctgcagc ctgaagattt tgcaacttat    660
tattgtcaac aatataatag ttaccctctc agtttcggcg agggaccaa ggtggagatc     720 aaacgt                                                              726

<210> SEQ ID NO 5
<211> LENGTH: 5
<212> TYPE: PRT
<213> ORGANISM: Artificial
<220> FEATURE:
<223> OTHER INFORMATION: translocation sequence

<400> SEQUENCE: 5

Arg Glu Asp Leu Lys
1               5

<210> SEQ ID NO 6
<211> LENGTH: 4
<212> TYPE: PRT
<213> ORGANISM: Artificial
<220> FEATURE:
<223> OTHER INFORMATION: translocation sequence

<400> SEQUENCE: 6

Arg Glu Asp Leu
1

<210> SEQ ID NO 7
<211> LENGTH: 4
<212> TYPE: PRT
<213> ORGANISM: Artificial
<220> FEATURE:
<223> OTHER INFORMATION: translocation sequence

<400> SEQUENCE: 7

Arg Asp Glu Leu
1

<210> SEQ ID NO 8
<211> LENGTH: 4
<212> TYPE: PRT
<213> ORGANISM: Artificial
<220> FEATURE:
<223> OTHER INFORMATION: translocation sequence

<400> SEQUENCE: 8

Lys Asp Glu Leu
1
```

INTERNALIZING ERBB2 ANTIBODIES

CROSS-REFERENCE TO RELATED APPLICATIONS

This application is a Continuation application from Ser. No. 13/441,651, filed Apr. 6, 2012; which claims benefit to Divisional application Ser. No. 12/928,792 (now U.S. Pat. No. 8,173,424), filed Dec. 16, 2010; which claims benefit to Divisional application Ser. No. 11/809,773 (Now U.S. Pat. No. 7,892,554), filed Jun. 1, 2007; which claims benefit application Ser. No. 09/250,056 filed Feb. 12, 1999 (now U.S. Pat. No. 7,244,826), which claims benefit under 35 U.S.C. §119(e) of provisional application U.S. Ser. No. 60/082,953, filed on Apr. 24, 1998, which is herein incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support awarded by the Department of Defense under Grants DAMD17-96-1-6244 and DAMD17-94-4433. The government of the United States of America has certain rights in the invention.

FIELD OF THE INVENTION

This invention pertains to the fields of immunodiagnostics and immunotherapeutics. More particularly this invention pertains to the discovery of novel human antibodies that specifically bind c-erbB-2, and to chimeric molecules containing these antibodies.

BACKGROUND OF THE INVENTION

It is generally desired to identify antibodies that specifically bind to particular classes of cells (e.g. tumor cells). Such antibodies, sometimes referred to as "targeting antibodies", can be used to specifically direct (deliver) various effector molecules (e.g. liposomes, cytotoxins, labels, etc.) to the target cell.

Targeting antibodies have been of particular interest in the study and treatment of cancer. A major goal of cancer research has been to identify tumor antigens that are qualitatively or quantitatively different from normal cells (Goldenberg (1994) *Ca: A Cancer J. for Clinicians.* 44: 43-64). The presence and/or quantity of such antigens could be detected by antibodies and such detection forms the basis of diagnostic and prognostic tests. In addition, the antibodies could be used to selectively kill tumor cells either directly via their effector function (Brown et al. (1989) *Blood.* 73: 651-661) or by attaching cytotoxic molecules to the antibody (Vitetta et al. (1987) *Science.* 238: 1098-1104; Brinkmann et al. (1993) *Proc. Natl. Acad. Sci. USA.* 90: 547-551).

Despite the demonstration of antigens that are overexpressed on tumor cells, antibodies have been used with limited success for diagnosis and treatment of solid tumors, (see review in Riethmuller et al. (1992) *Curr. Opin. Immunol.* 4: 647-655, and Riethmuller (1993) *Curr. Opinion Immunol.* 5: 732-739). Their utility has been hampered by the paucity of tumor specific antibodies, antibody immunogenicity, low binding affinity, and poor tumor penetration.

Nonspecific toxicity results from the failure of the antibody to bind specifically and with high affinity to tumor cells. As a result, nonspecific cell killing occurs. In addition, the foreign immunotoxin molecule elicits a strong immune response in humans. The immunogenicity of the toxin portion of the immunotoxin has recently been overcome by using the human analogue of RNase (Rybak et al. (1992) *Proc. Nat. Acad. Sci., USA,* 89: 3165). The murine antibody portion, however, is still significantly immunogenic (Sawler et al., (1995) *J. Immunol.,* 135: 1530).

Immunogenicity could be avoided and toxicity reduced if high affinity tumor specific human antibodies were available. However, the production of human monoclonal antibodies using conventional hybridoma technology has proven extremely difficult (James et al., (1987) *J. Immunol. Meth.,* 100: 5). Furthermore, the paucity of purified tumor-specific antigens makes it necessary to immunize with intact tumor cells or partially purified antigen. Most of the antibodies produced react with antigens that are also common to normal cells and are therefore unsuitable for use as tumor-specific targeting molecules.

SUMMARY OF THE INVENTION

This invention provides two new internalizing anti-cerbB-2 antibodies designated herein as F5 (encoded by ATCC plasmid deposit PTS-7843) and C1 respectively. Preferred antibodies specifically bind to a c-erbB2 receptor and are antibody F5-derived or C1-derived antibodies (i.e., antibodies that bind to a c-erbB2 receptor epitope bound by F5 and/or C1). The antibodies preferably comprise an amino acid sequence selected from the group consisting of SEQ ID NO: 1, SEQ ID NO: 2, SEQ ID NO: 1 having conservative substitutions, and SEQ ID NO: 2 having conservative substitutions. Particularly preferred antibodies share at least 70% sequence identity with the amino acid sequence of SEQ ID NO: 1 or SEQ ID NO: 2 and have a binding affinity for c-erbB2 on cells of at least $10^{-5}$M. In one embodiment the antibodies will have an amino acid sequence that differs from the amino acid sequence of SEQ ID NO: 1 or SEQ ID NO: 2 by no more than 30 residues. The antibody can comprise at least one, at least two or at least three of the complementarity determining regions (CDRs) of SEQ ID NO: 1 and/or SEQ ID NO: 2. In addition, or alternatively, the antibody can comprise at least one, at least two, or at least three framework regions of SEQ ID NO: 1 and/or SEQ ID NO: 2. Particularly preferred F5 and C1 antibodies have the amino acid sequence of SEQ ID NO: 1 or SEQ ID NO: 2, respectively.

In another embodiment, this invention provides for antibodies that are cross-reactive with an anti-idiotypic antibody raised against F5 or C1. Thus, this invention provides for an antibody that specifically binds to a c-erbB2 receptor, where the antibody comprises at least 10 contiguous amino acids from the polypeptide sequence as set forth in SEQ ID NO: 1 or SEQ ID NO: 2, and where the antibody, when presented as an antigen, elicits the production of an anti-idiotypic antibody that specifically binds to a polypeptide sequence as set forth in SEQ ID NO: 1 or SEQ ID NO: 2; and the antibody does not bind to antisera raised against the polypeptide set forth in SEQ ID NO: 1 and SEQ ID NO: 2, that has been fully immunosorbed with the polypeptides set forth in SEQ ID NO: 1 and in SEQ ID NO: 2. These antibodies can share at least 70% sequence identity with the amino acid sequence of SEQ ID NO: 1 or SEQ ID NO: 2 and have a binding affinity for c-erbB2 on cells of at least $10^{-5}$M (10 µM). The antibody may comprise an amino acid sequence that differs from the amino acid sequence of SEQ ID NO: 1 or SEQ ID NO: 2 by no more than 30 residues. The antibody may comprise a complementarity determining region (CDR) of SEQ ID NO: 1 or SEQ ID NO: 2

This invention also provides for the epitopes specifically recognized by F5 or C1. These are easily identified by epitope mapping methods utilizing the F5 or C1 antibodies provided herein.

In still another embodiment, this invention provides methods of specifically delivering an effector molecule to a cell bearing a c-erbB2 receptor. The methods involve providing a chimeric molecule comprising the effector molecule attached to any of the C1-derived or F5-derived antibodies described herein and contacting the cell bearing a c-erbB2 with the chimeric molecule, whereby the chimeric molecule specifically binds to the cell. In a particularly preferred embodiment, all, or a portion of the chimeric molecule is internalized into the cell. Preferred effector molecules include, but are not limited to, cytotoxins, labels, radionuclides, drugs, liposomes, ligands, antibodies, and the like. In a particularly preferred embodiment, the effector molecule is a protein or contains a protein and the chimeric molecule is a fusion protein. Particularly preferred target cells are cancer (e.g. metastatic or solid tumor, e.g. breast cancer) cells This invention also provides for the chimeric molecules that comprise any of the antibodies described herein attached to any of the effector molecules described herein. Preferred chimeric molecules bind a cell bearing a c-erbB-2. Particularly preferred chimeric molecules are fusion proteins.

This invention also provides for nucleic acids encoding the various constructs described herein. Thus, in one embodiment, this invention provides nucleic acids encode an antibody that specifically binds to a c-erbB2 receptor, where the antibody is an F5-derived or a C1-derived antibody that specifically binds to the epitope bound by F5 (SEQ ID NO: 1) or C1 (SEQ ID NO: 2). Preferred nucleic acids encode an amino acid sequence selected from the group consisting of SEQ ID NO: 1, SEQ ID NO: 2, SEQ ID NO: 1 having conservative substitutions, and SEQ ID NO: 2 having conservative substitutions. Particularly preferred nucleic acids hybridize with a nucleic acid that encodes the antibodies of SEQ ID NO: 1 or SEQ ID NO: 2 under stringent conditions. Other preferred nucleic acids encode an antibody that shares at least 70% sequence identity with the amino acid sequence of SEQ ID NO: 1 or SEQ ID NO: 2 and wherein said antibody has a binding affinity for -erbB2 on cells of at least 10 µM. Particularly preferred nucleic acids encodes an amino acid sequence that differs from the amino acid sequence of SEQ ID NO: 1 or SEQ ID NO: 2 by no more than 30 residues. Another preferred nucleic acid encodes one or more complementarity determining regions (CDRs) of SEQ ID NO: 1 or SEQ ID NO: 2. Other preferred nucleic acids comprise a sequence encoding the amino acid sequence of SEQ ID NO: 1 or SEQ ID NO: 2.

Where the chimeric proteins are fusion proteins this invention also provides nucleic acids encoding the chimeric proteins.

In another embodiment, this invention provides for cells (e.g. eukaryotic or prokaryotic) expressing any of the nucleic acids described herein.

This invention also provides for pharmaceutical compositions. The pharmaceutical compositions preferably comprise a pharmacological excipient and one or more of the F5-derived or C1-derived antibodies described herein.

Kits are also provides as described herein for the diagnosis and treatment of pathological conditions (e.g. cancers) or for the practice of any of the screening or transfection methods described herein.

DEFINITIONS

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the F(ab)'2 dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci USA*, 85:5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see e.g., U.S. Pat. Nos. 5,091,513; 5,132,405; and 4,956,778). Particularly preferred antibodies include all those that have been displayed on phage (e.g., scFv, Fv, Fab and disulfide linked Fv) (Reiter et al. (1995) *Protein Eng.* 8: 1323-1331).

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

An "internalizing antibody" is an antibody that, upon binding to a receptor or other ligand on a cell surface is transported into the cell (e.g. into a vacuole or other organelle or into the cytoplasm of the cell).

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the dissociation constant $K_d$ (see, generally, Davies et al. (1990) *Ann. Rev. Biochem.*, 59: 439473).

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, F5 or C1 antibodies can be raised to the c-erbB-2 protein that bind c-erbB-2 and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The terms "polypeptide", "peptide", or "protein" are used interchangeably herein to designate a linear series of amino acid residues connected one to the other by peptide bonds between the alpha-amino and carboxy groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR §1.822(b)(4). Furthermore, it should be noted that a dash at the beginning or end of an amino acid residue sequence indicates either a peptide bond to a further sequence of one or more amino acid residues or a covalent bond to a carboxyl or hydroxyl end group.

The term "binding polypeptide" refers to a polypeptide that specifically binds to a target molecule (e.g. a cell receptor) in a manner analogous to the binding of an antibody to an antigen. Binding polypeptides are distinguished from antibodies in that binding polypeptides are not ultimately derived from immunoglobulin genes or fragments of immunoglobulin genes.

The terms "F5 antibody" or "C1 antibody" typically refer to antibodies that bind to the epitope(s) bound by F5 or C1 respectively. Preferred F5 or C1 antibodies are internalizing antibodies. F5 and C1 when used to refer to the prototypical antibody refer to antibodies having the sequence of SEQ ID NO: 1 and SEQ ID NO: 2, respectively. The F5 antibody is also referred to as 3TF5 in the examples.

The term "conservative substitution" is used in reference to proteins or peptides to reflect amino acid substitutions that do not substantially alter the activity (specificity or binding affinity) of the molecule. Typically conservative amino acid substitutions involve substitution one amino acid for another amino acid with similar chemical properties (e.g. charge or hydrophobicity). The following six groups each contain amino acids that are typical conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated.

Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605-2608; and Cassol et al. (1992); Rossolini et al., (1994) *Mol. Cell. Probes* 8: 91-98). The term nucleic acid is used interchangeably with gene, cDNA, and mRNA encoded by a gene.

The terms "isolated" or "biologically pure" refer to material which is substantially or essentially free from components which normally accompany it as found in its native state. However, the term "isolated" is not intended refer to the components present in an electrophoretic gel or other separation medium. An isolated component is free from such separation media and in a form ready for use in another application or already in use in the new application/milieu.

The terms "identical" or percent "identity," or percent "homology" in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90-95% or even at least 98% amino acid residue identity across a window of at least 30 nucleotides, preferably across a window of at least 40 nucleotides, more preferably across a window of at least 80 nucleotides, and most preferably across a window of at least 100 nucleotides, 150 nucleotides, 200 nucleotides or greater, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215:403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrases "hybridizing specifically to" or "specific hybridization" or "selectively hybridize to", refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.) supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The terms F5 and C1 when referring to antibodies refer to the antibodies of SEQ ID NOs: 1 and 2, respectively. Preferred F5 and C1 antibodies additionally include the antibodies of SEQ ID NOs: 1 and 2, respectively, or conservative substitutions of these sequences so long as the binding specificity of F5 and C1 is preserved. The F5-derived and C1-derived antibodies are antibodies derived sequences (from the amino acid or nucleic acid) of F5 or C1, respectively. The F5- and C1-derived antibodies are preferably obtained by one of several types of derivation that include, but are not limited to: 1) derivation by chain shuffling; 2) derivation by site directed mutagenesis of CDRs; 3) derivation by introducing multiple mutations into sequence by either error prone PCR, mutator strains of *E. coli*, or "DNA shuffling (Crameri et al. (1996) *Nature* 65 *Medicine.* 2: 100-102). The F5 and C1 derived antibodies are recognized by their cross-reactivity with either 1) the c-erbB-2 epitope recognized by F5 and C1; and/or 2) An anti F5 or C1 anti-idiotypic antibody. F5 and C1 antibodies preferably have a binding affinity of about 2 µM more preferably of less than about 1 µM and most preferably of less than about 100 nM or better and are preferably derived by screening (for affinity the epitopes bound by F5 and C1, respectively) a phage display library in which a known F5 or C1 variable heavy (VH) chain is expressed in combination with a multiplicity of variable light (VL) chains or conversely a known F5 or C1 variable light chain is expressed in combination with a multiplicity of variable heavy (VH) chains. F5- or C1-derived antibodies also include those antibodies produced by the introduction of mutations into the variable heavy or variable light complementarity determining regions (CDR1, CDR2 or CDR3) as described herein. Finally F5 and C1 antibodies include those antibodies produced by any combination of these modification methods as applied to F5 or CI and their derivatives.

A chimeric molecule is a molecule in which two or more molecules that exist separately in their native state are joined together to form a single molecule having the desired functionality of all of its constituent molecules. While the chimeric molecule may be prepared by covalently linking two molecules each synthesized separately, one of skill in the art will appreciate that where the chimeric molecule is a fusion protein, the chimera may be prepared de novo as a single "joined" molecule.

A fusion protein is a chimeric molecule in which the constituent molecules are all polypeptides and are attached (fused) to each other through terminal peptide bonds so that the chimeric molecule is a continuous single-chain polypeptide. The various constituents can be directly attached to each other or can be coupled through one or more peptide linkers.

An effector moiety or molecule is a molecule or moiety that typically has a characteristic activity that is desired to be delivered to a target cell (e.g. a tumor overexpressing c-erbB-2). Effector molecules include cytotoxins, labels, radionuclides, ligands, antibodies, drugs, liposomes, and viral coat proteins that render the virus capable of infecting a c-erbB-2 expressing cell.

A "target" cell refers to a cell or cell-type that is to be specifically bound by a member of a phage display library or a chimeric molecule of this invention. Preferred target cells are cells for which an internalizing antibody or binding polypeptide is sought. The target cell is typically characterized by the expression or overexpression of a target molecule that is characteristic of the cell type. Thus, for example, a target cell can be a cell, such as a tumor cell, that overexpresses a marker such as c-erbB-2.

A "targeting moiety" refers to a moiety (e.g. a molecule) that specifically binds to the target molecule. Where the target molecule is a molecule on the surface of a cell and the targeting moiety is a component of a chimeric molecule, the targeting moiety specifically binds the chimeric molecule to the cell bearing the target. Where the targeting moiety is a polypeptide it can be referred to as a "targeting polypeptide".

The terms "internalizing" or "internalized" when used in reference to a cell refer to the transport of a moiety (e.g. phage) from outside to inside a cell. The internalized moiety can be located in an intracellular compartment, e.g. a vacuole, a lysosome, the endoplasmic reticulum, the golgi apparatus, or in the cytosol of the cell itself.

An internalizing receptor or marker is a molecule present on the external cell surface that when specifically bound by an antibody or binding protein results in the internalization of that antibody or binding protein into the cell. Internalizing receptors or markers include receptors (e.g., hormone, cytokine or growth factor receptors) ligands and other cell surface markers binding to which results in internalization.]

The term "heterologous nucleic acid' refers to a nucleic acid that is not native to the cell in which it is found or whose ultimate origin is not the cell or cell line in which the "heterologous nucleic acid" is currently found.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen. Anti-idiotypic antibodies can also be generated by immunization with an antibody, or fragment thereof.

A "phage display library" refers to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable of displaying a heterogenous polypeptide on its surface. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. The filamentous phage may contains a selectable marker such as tetracycline (e.g., "fd-tet"). Various filamentous phage display systems are well known to those of skill in the art (see, e.g., Zacher et al. (1980) *Gene* 9: 127-140, Smith et al. (1985) *Science* 228: 1315-1317 (1985); and Parmley and Smith (1988) *Gene* 73: 305-318).

A "viral packaging signal" is a nucleic acid sequence necessary and sufficient to direct incorporation of a nucleic acid into a viral capsid.

An assembly cell is a cell in which a nucleic acid can be packaged into a viral coat protein (capsid). Assembly cells may be infected with one or more different virus particles (e.g. a normal or debilitated phage and a helper phage) that individually or in combination direct packaging of a nucleic acid into a viral capsid.

The following abbreviations are used herein: AMP, ampicillin; c-erbB-2 ECD, extracellular domain of c-erbB-2; CDR, complementarity determining region; ELISA, enzyme linked immunosorbent assay; FACS, fluorescence activated cell sorter; FR, framework region; Glu, glucose; HBS, hepes buffered saline, 10 mM hepes, 150 mM NaCl, pH 7.4; IMAC, immobilized metal affinity chromatography; $k_{on}$, association rate constant; $k_{off}$, dissociation rate constant; MPBS, skimmed milk powder in PBS; MTPBS, skimmed milk powder in TPBS; PBS, phosphate buffered saline, 25 mM $NaH_2PO_4$, 125 mM NaCl, pH 7.0; PCR, polymerase chain reaction; RU, resonance units; scFv or scFv, single-chain Fv fragment; TPBS, 0.05% v/v Tween 20 in PBS; SPR, surface plasmon resonance; $V_k$, immunoglobulin kappa light chain variable region; $V_\lambda$, immunoglobulin lambda light chain variable region; $V_L$, immunoglobulin light chain variable region; $V_H$, immunoglobulin heavy chain variable region; wt, wild type.

DETAILED DESCRIPTION

I. Introduction

Figure 1:
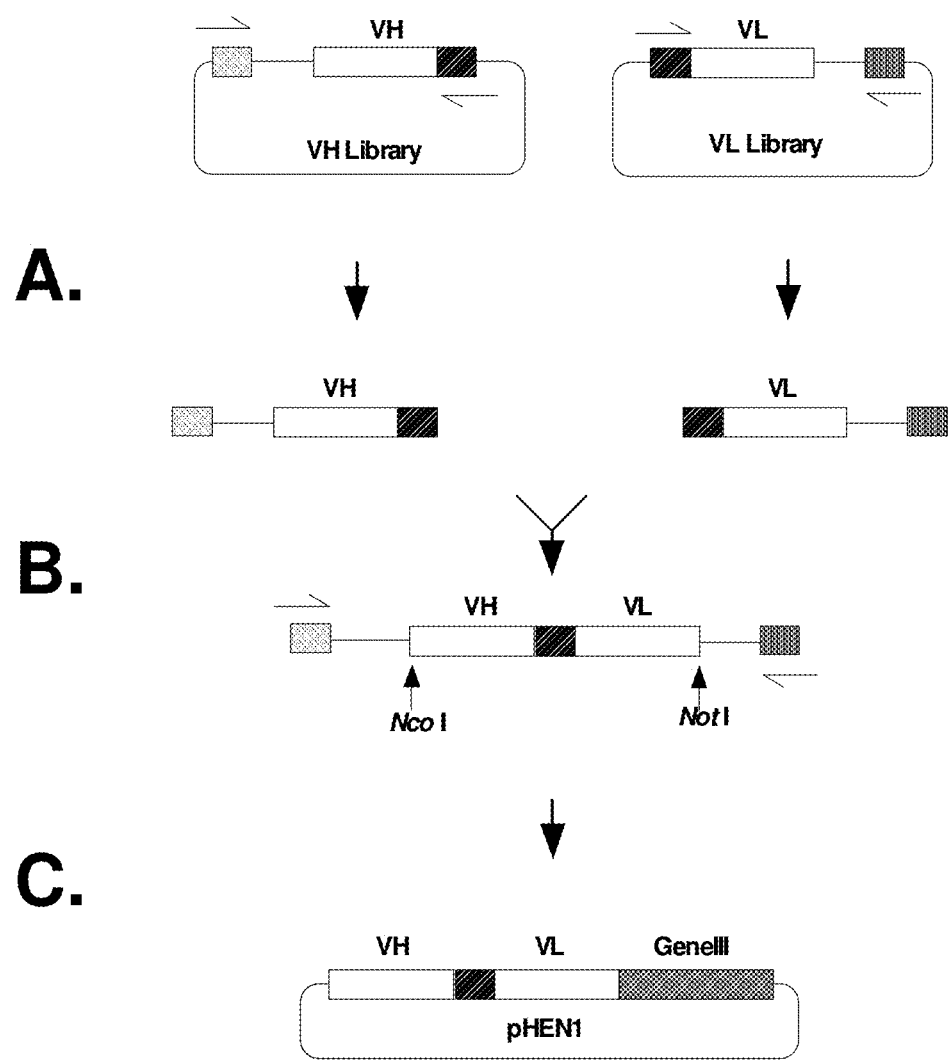
FIG. 1 illustrates the method for construction of a large human scFv phage antibody library. The strategy for library construction involved optimizing the individual steps of library construction to increase both the efficiency of scFv gene assembly and to increase the efficiency of cloning assembled scFv genes. (A). First, mRNA from lymphocytes was used to generate $V_H$ and $V_L$ gene repertoires by RTPCR which were cloned into different vectors to create $V_H$ and $V_L$ gene libraries of $8.0 \times 10^8$ and $7.2 \times 10^6$ members respectively. The cloned V-gene libraries provided a stable and limitless source of $V_H$ and $V_L$ genes for scFv assembly. DNA encoding the peptide $(G_4S)_3$ was incorporated into the 5' end of the $V_L$ library. This permitted generation of scFv genes by PCR splicing 2 DNA fragments. Previously, scFv gene repertoires were assembled from 3 separate DNA fragments consisting of $V_H$, $V_L$, and linker DNA. (B) $V_H$ and $V_L$ gene repertoires were amplified from the separate libraries and assembled into an scFv gene repertoire using overlap extension PCR. The primers used to reamplify the $V_H$ and $V_L$ gene repertoires annealed 200 bp upstream of the 5' end of the $V_H$ genes and 200 bp down stream of the $V_L$ genes. These long overhangs ensured efficient restriction enzyme digestion. (C.) The scFv gene repertoire was digested with NcoI and NotI and cloned into the plasmid pHEN1 as fusions with the M13 gene III coat protein gene ( ) for phage-display.

This invention provides for novel human antibodies that specifically bind to the extracellular domain of the c-erbB-2 protein product of the HER2/neu oncogene. The c-erbB-2 marker is overexpressed by 30-50% of breast carcinomas and other adenocarcinomas and thus provides a useful cell surface marker for specifically targeting tumor cells such as carcinomas. In contrast to previous known anti-cerbB-2 antibodies, the antibodies of the present invention (designated herein as F5 or C1 antibodies) are fully human antibodies. Thus, administration of these antibodies to a human host elicits a little or no immunogenic response.

In addition, the F5 and C1 antibodies of this invention are rapidly internalized into the cell. They are thus extremely useful for delivering effector moieties into the target cell. Moreover, once an internalizing antibody or polypeptide is identified it can be used to re-probe one or more cells or cell lines to identify previously unknown internalizing cellular targets (e.g., receptors).

It is known that other c-erbB2-binding antibodies are not internalized. Thus, without being bound to particular theory, it is believed that the effective internalization of the F5 and C1 antibodies of this invention is a consequence of the specific epitope bound by these antibodies. It is believed that both the F5 and C1 antibody bind the same epitope and, using the F5 and C1 antibodies identified herein (e.g. SEQ ID NOS: 1 and 2) other antibodies that bind to the same epitope can be readily identified. Thus, in one preferred embodiment, this invention provides an antibody that specifically binds to a c-erbB2 receptor epitope bound by F5 or C1. Particularly preferred antibodies of this type are internalizing antibodies.

Because of the highly specific targeting to cells expression the c-erbB2 receptor and the effective internalization of the bound molecules, the C1 and F5 antibodies of this invention are well suited for delivering effector molecules to or into a target cell (e.g. a cancer cell). Thus, in another preferred embodiment, this invention additionally provides for chimeric molecules comprising the F5 or C1 antibodies (i.e.

antibodies that bind to the epitope bound by F5 or C1) joined to an effector molecule. The F5 or C1 antibody acts as a targeting molecule that serves to specifically bind the chimeric molecule to cells bearing the c-erbB-2 marker thereby delivering the effector molecule to the target cell.

An effector is a molecule or multimolecular structure (e.g. a liposome, a phage coat (capsid), or an intact phage) that is desired to be delivered to the target cell (e.g. a tumor overexpressing c-erbB-2). Preferred effectors have a characteristic activity (e.g. drug delivery, cytotoxicity, fluorescence, radioactivity, etc.) Effector molecules include, but are not limited to, cytotoxins, labels, radionuclides, ligands, antibodies, drugs, nucleic acids, hormones, growth factors, liposomes, and viral coat proteins that render a virus capable of infecting a c-erbB-2 expressing cell. Once delivered to the target, the effector molecule exerts its characteristic activity.

For example, in one embodiment, where the effector molecule is a cytotoxin, the chimeric molecule acts as a potent cell-killing agent specifically targeting the cytotoxin to tumor cells bearing the c-erbB-2 marker. Chimeric cytotoxins that specifically target tumor cells are well known to those of skill in the art (see, for example, Pastan et al. (1992) *Ann. Rev. Biochem.*, 61: 331-354).

In another embodiment, the chimeric molecule may be used for detecting the presence or absence of tumor cells in vivo or in vitro or for localizing tumor cells in vivo. These methods involve providing a chimeric molecule comprising an effector molecule, that is a detectable label. The C1 or F5 antibodies specifically bind the chimeric molecule to tumor cells expressing the c-erbB-2 marker which are then marked by their association with the detectable label. Subsequent detection of the cell-associated label indicates the presence and/or mass and/or location of a tumor cell.

In yet another embodiment, the effector molecule may be another specific binding moiety including, but not limited to an antibody, an antigen binding domain, a growth factor, or a ligand. The chimeric molecule will then act as a highly specific bifunctional linker. This linker may act to bind and enhance the interaction between cells or cellular components to which the chimeric protein binds. Thus, for example, where the "effector" component is an anti-receptor antibody or antibody fragment, the C6 antibody component specifically binds c-erbB-2 bearing cancer cells, while the effector component binds receptors (e.g., IL-2, IL-4, FcI, FcII and FcIII receptors) on the surface of immune cells. The chimeric molecule may thus act to enhance and direct an immune response toward target cancer cells.

In still yet another embodiment the effector molecule may be a pharmacological agent (e.g. a drug). Thus the C1 or F5 antibody may be conjugated to a drug such as vinblastine, vindesine, melphalan, N-acetylmelphalan, methotrexate, aminopterin, doxirubicin, daunorubicin, genistein (a tyrosine kinase inhibitor), an antisense molecule, and other pharmacological agents known to those of skill in the art, thereby specifically targeting the pharmacological agent to tumor cells expressing c-erbB-2.

Alternatively, the F5 or C1 antibodies may be bound to a vehicle containing the therapeutic composition. Such vehicles include, but are not limited to liposomes, micelles, various synthetic beads, and the like.

One of skill in the art will appreciate that the chimeric molecules of the present invention optionally includes multiple targeting moieties (F5 and/or C1 antibodies) bound to a single effector or conversely, multiple effector molecules bound to a single targeting moiety. In still other embodiment, the chimeric molecules include both multiple targeting moieties and multiple effector molecules. Thus, for example, this invention provides for "dual targeted" cytotoxic chimeric molecules in which the F5 or C1 antibody is attached to a cytotoxic molecule while another molecule (e.g. an antibody, or another ligand) is attached to the other terminus of the toxin. Such a dual-targeted cytotoxin might comprise, e.g. an F5 or C1 antibody substituted for domain Ia at the amino terminus of a PE and anti-TAC(Fv) inserted in domain III. Other antibodies may also be suitable effector molecules.

As indicated above, preferred F5 and C1 antibodies of this invention are internalizing antibodies. Often such internalizing antibodies have a biological activity even without the presence of an effector molecule. Many receptors (for example growth factor receptors) use internalization as a way of modulating and regulating the effect of ligands. For example, ligand binding can result in signal transduction and receptor internalization. The decrease in the number of receptors then causes down regulation of the effect of additional ligand. The same occurs with antibodies that bind growth factor receptors (Hurwitz et al. (1995) *Proc. Natl. Acad. Sci. USA*. 92: 3353-3357). For example, "[g]rowth factors act by binding to and activating the intrinsic catalytic activity of their cell surface receptors, thereby initiating a signaling cascade leading to the cellular response. Growth factor/receptor complexes are not static residents of the cell surface membrane but undergo endocytic trafficking processes of internalization and sorting to recycling or degradation. Consequently, growth factors are depleted from the extracellular medium and their receptors undergo down-regulation. These trafficking processes, by virtue of their influence on the kinetics of signaling growth factor/receptor complexes, are important modulators of cell behavioral responses" (Reddy et al. (1996) *Nature Biotech.* 14: 1696-1699)

In the ErbB2 system, one mechanism by which ErbB2 binding antibodies inhibit growth is to cause receptor internalization and down regulation (Hurwitz et al. (1995) *Proc. Natl. Acad. Sci. USA*. 92: 3353-3357). It also may be possible to turn an internalizing antibody that binds a growth factor receptor into a growth inhibitor or stimulatory antibody. For example, the mitogenic properties of EGF have been increased by lowering the affinity of EGF for the EGF receptor. The lower affinity EGF causes receptor signaling, but reduced internalization and down regulation than wild type EGF (presumably from the lower affinity) (Reddy et al. (1996) *Nature Biotech.* 14: 1696-1699). Thus lowering the affinity of a C1 or F5 internalizing antibody could turn it into a growth factor. The F5 and C1 internalizing antibodies of this invention can provide lead compounds/drugs for both growth inhibition and growth stimulation.

II. Preparation/Synthesis of F5 and C1 Antibodies

Using the sequence information provided herein (SEQ ID NO: 1, SEQ ID NO: 2, SEQ ID NO: 3, SEQ ID NO: 4), the explicitly listed F5 and C1 antibodies can be routinely created either by de novo chemical synthesis or by recombinant DNA expression techniques. Similarly modified F5 and C1 antibodies identified according to the methods as well as the chimeric molecules of this invention can be synthesized de novo or recombinantly expressed (particularly where the chimeric molecule is a fusion protein.

A) Chemical Synthesis.

The F5 and C1 antibodies of this invention can be chemically synthesized using well known methods of peptide synthesis. Solid phase synthesis in which the C-terminal amino acid of the sequence is attached to an insoluble support followed by sequential addition of the remaining amino acids in the sequence one preferred method for the chemical synthesis of C1 and F5 antibodies. Techniques for solid phase synthesis are described by Barany and Merrifield, *Solid Phase Peptide Synthesis*; pp. 3-284 in *The Peptides: Analysis, Synthesis, Biology.* Vol. 2: *Special Methods in Peptide Synthesis*, Part A., Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

Typically F5 and C1 antibodies are chemically synthesized using an automated peptide synthesizer such as an Eppendorf Synostat (Madison, Wis.) or a Milligen 9050 (Milford, Mass.), although manual methods of composition peptide synthesis also can be used. In one embodiment, synthesis is on a polyethylene glycolpolystyrene (PEG-PS) graft resin and using $N^\alpha$-Fmoc amino acid derivatives as described in U.S. Pat. No. 5,547,939. Other resins and synthesis chemistries (e.g. T-boc) can be used.

B) Recombinant Expression.

In a preferred embodiment, the F5 or C1 antibodies of this invention are prepared using standard techniques well known to those of skill in the art in combination with the polypeptide and nucleic acid sequences provided herein. The polypeptide sequences may be used to determine appropriate nucleic acid sequences encoding the particular F5 or C1 antibody disclosed thereby. The nucleic acid sequence may be optimized to reflect particular codon "preferences" for various expression systems according to standard methods well known to those of skill in the art. Alternatively, the nucleic acid sequences provided herein may also be used to express F5 or C1 antibodies.

Using the sequence information provided, the nucleic acids may be synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (Beaucage et. al. (1981) *Tetrahedron Letts.* 22(20): 1859-1862).

Once a nucleic acid encoding a F5 or C1 antibody is synthesized it may be amplified and/or cloned according to standard methods. Molecular cloning techniques to achieve these ends are known in the art. A wide variety of cloning and in vitro amplification methods suitable for the construction of recombinant nucleic acids, e.g., encoding F5 or C1 antibody genes, are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033.

Examples of techniques sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 15 1874; Lomeli et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117 Improved methods of cloning in vitro amplified nucleic acids are described in Wallace et al., U.S. Pat. No. 5,426,039.

Once the nucleic acid for a F5 or C1 antibody is isolated and cloned, one may express the gene in a variety of recombinantly engineered cells known to those of skill in the art. Examples of such cells include bacteria, yeast, filamentous fungi, insect (especially employing baculoviral vectors), and mammalian cells. It is expected that those of skill in the art are knowledgeable in the numerous expression systems available for expression of F5 or C1 antibodies.

In brief summary, the expression of natural or synthetic nucleic acids encoding F5 or C1 antibodies will typically be achieved by operably linking a nucleic acid encoding the antibody to a promoter (which is either constitutive or inducible), and incorporating the construct into an expression vector. The vectors can be suitable for replication and/or integration in prokaryotes, eukaryotes, or both. Typical cloning vectors contain transcription and translation terminators, initiation sequences, and promoters useful for regulation of the expression of the nucleic acid encoding the F5 or C1 antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook, supra.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024 and the leftward promoter of phage lambda ($P_L$) as described by Herskowitz and Hagen (1980) *Ann. Rev. Genet.*, 14: 399-445. The inclusion of selection markers in DNA vectors transformed in *E. coli* is also useful. Examples of such markers include genes specifying resistance to ampicillin, tetracycline, or chloramphenicol. See Sambrook for details concerning selection markers, e.g., for use in *E. coli*.

Expression systems for expressing F5 or C1 antibodies are available using *E. coli, Bacillus* sp. (Palva et al. (1983) *Gene* 22:229-235; Mosbach, et al., *Nature*, 302:543-545) and *Salmonella. E. coli* systems are preferred.

The F5 or C1 antibodies produced by prokaryotic cells may require exposure to chaotropic agents for proper folding. During purification from, e.g., *E. coli*, the expressed protein is optionally denatured and then renatured. This is accomplished, e.g., by solubilizing the bacterially produced antibodies in a chaotropic agent such as guanidine HCl. The antibody is then renatured, either by slow dialysis or by gel filtration. See, U.S. Pat. No. 4,511,503.

Methods of transfecting and expressing genes in mammalian cells are known in the art. Transducing cells with nucleic acids can involve, for example, incubating viral vectors containing F5 or C1 nucleic acids with cells within the host range of the vector. See, e.g., *Methods in Enzymology*, vol. 185, Academic Press, Inc., San Diego, Calif. (D. V. Goeddel, ed.)

(1990) or M. Krieger, *Gene Transfer and Expression—A Laboratory Manual*, Stockton Press, New York, N.Y., (1990) and the references cited therein.

The culture of cells used in the present invention, including cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of cells.

Techniques for using and manipulating antibodies are found in Coligan (1991) *Current Protocols in Immunology Wiley/Greene*, NY; Harlow and Lane (1989) *Antibodies: A Laboratory Manual Cold Spring Harbor Press*, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

In one preferred embodiment the F5 or C1 antibody gene is subcloned into an expression vector, e.g., pUC119Sfi/NotHismyc (Schier et al. (1995) *Immunotechnology*. 1: 63-71). This results in the addition of a hexa-histidine tag at the C-terminal end of the scFv. A pHEN-1 vector DNA containing the F5 or C1 scFv DNA is prepared by alkaline lysis miniprep, digested with NcoI and NotI, and the scFv DNA purified on a 1.5% agarose gel. The F5 or C1 scFv DNA is ligated into pUC119Sfi1/Not1Hismyc digested with NcoI and NotI and the ligation mixture used to transform electro-competent *E. coli* HB2151. For expression, 200 ml of 2×TY media containing 100 ㎍/ml ampicillin and 0.1% glucose is inoculated with *E. coli* HB2151 harboring the F5 or C1 gene in pUC119Sfi1/Not1Hismyc. The culture is grown at 37° C. to an $A_{600}$ nm of 0.8. Soluble scFv is expression induced by the addition of IPTG to a final concentration of 1 mM, and the culture is grown at 30° C. in a shaker flask overnight.

The F5 or C1 antibodies may then be harvested from the periplasm using the following protocol: Cells are harvested by centrifugation at 4000 g for 15 min, resuspended in 10 ml of ice cold 30 mM Tris-HCl pH 8.0, 1 mM EDTA, 20% sucrose, and incubated on ice for 20 minutes. The bacteria are then pelleted by centrifugation at 6000 g for 15 min. and the "periplasmic fraction" cleared by centrifugation at 30,000 g for 20 mM The supernatant is then dialyzed overnight at 4° C. against 8 L of IMAC loading buffer (50 mM sodium phosphate pH 7.5, 500 mM NaCl, 20 mM imidazole) and then filtered through a 0.2 micron filter.

In a preferred embodiment, the F5 and/or C1 scFv is purified by IMAC. All steps are preferably performed at 4° C. A column containing 2 ml of Ni-NTA resin (Qiagen) is washed with 20 ml IMAC column wash buffer (50 mM sodium phosphate pH 7.5, 500 mM NaCl, 250 mM imidazole) and 20 ml of IMAC loading buffer. The periplasmic preparation is then loaded onto the column and the column washed sequentially with 50 ml IMAC loading buffer and 50 ml IMAC washing buffer (50 mM sodium phosphate pH 7.5, 500 mM NaCl, 25 mM imidazole). Protein was eluted with 25 ml IMAC elution buffer (50 mM sodium phosphate pH 7.5, 500 mM NaCl, 100 mM imidazole) and 4 ml fractions collected. The F5 and C1 antibody may be detected by absorbance at 280 nm and scFv fraction eluted. To remove dimeric and aggregated scFv, samples can be concentrated to a volume <1 ml in a Centricon 10 (Amicon) and fractionated on a Superdex 75 column using a running buffer of HBS (10 mM Hepes, 150 mM NaCl, pH 7.4).

The purity of the final preparation may be evaluated by assaying an aliquot by SDS-PAGE. The protein bands can be detected by Coomassie staining. The concentration can then be determined spectrophotometrically, assuming that an $A_{280}$ nm of 1.0 corresponds to an scFv concentration of 0.7 mg/ml.

III. Modification of and/or Selection of Modified F5 and C1 Antibodies

In a preferred embodiment, generation of new (different) F5 or C1 antibodies involves generating an antibody (e.g. whole antibody, antibody fragment, or single chain antibody) and then screening the antibody to verify that it is an F5 or C1 antibody (i.e. that it binds the epitope bound by F5 or C1 and more preferably that it is internalized). The antibodies to be screened can be randomly generated by a variety of means, produced in vivo (e.g. by immunization of an animal with a c-erbB2 epitope), or produced ex vivo, e.g. in a phage, or other, display library. The antibodies thus produced are then screened for c-erbB2 binding affinity and/or for specific binding to an F5 or C1 epitope, and/or for internalization into a cell bearing the c-erbB2 receptor or fragment(s) thereof.

A) Generation of F5- and C1-Derived Antibodies for Screening.

Alternatively the F5- and C1-derived antibodies are preferably obtained by one of several strategies utilizing the F5 and C1 sequences provided herein. Such methods include, but are not limited to: 1) derivation by chain shuffling; 2) derivation by site directed mutagenesis of CDRs; 3) derivation by introducing multiple mutations into sequence by either error prone PCR, mutator strains of *E. coli*, or "DNA shuffling". These derived antibodies include 'library approaches' where libraries of mutant sequences based on F5 or C1 are created and binding function is then selected for.

1) Generation of Phage-Display Libraries

The ability to express antibody fragments on the surface of viruses that infect bacteria (bacteriophage or phage) makes it possible to isolate a single binding antibody fragment from a library of greater than $10^{10}$ nonbinding clones. To express antibody fragments on the surface of phage (phage display), an antibody fragment gene is inserted into the gene encoding a phage surface protein (pIII) and the antibody fragment-pIII fusion protein is displayed on the phage surface (McCafferty et al. (1990) *Nature,* 348: 552-554; Hoogenboom et al. (1991) *Nucleic Acids Res.* 19: 4133-4137). Since the antibody fragments on the surface of the phage are functional, phage bearing antigen binding antibody fragments can be separated from non-binding phage by antigen affinity chromatography (McCafferty et al. (1990) *Nature,* 348: 552-554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature,* 348: 552-554). Thus even when enrichments are low (Marks et al. (1991) *J. Mol. Biol.* 222: 581-597), multiple rounds of affinity selection can lead to the isolation of rare phage. Since selection of the phage antibody library on antigen results in enrichment, the majority of clones bind antigen after four rounds of selection. Thus only a relatively small number of clones (several hundred) need to be analyzed for binding to antigen. It is noted that in certain preferred embodiments, polyvalent phage display systems are preferred as indicated in the Examples.

In a preferred embodiment, analysis for binding is simplified by including an amber codon between the antibody fragment gene and gene III. The amber codon makes it possible to easily switch between displayed and soluble (native) antibody fragment simply by changing the host bacterial strain (Hoogenboom et al. (1991) *Nucleic Acids Res.* 19: 4133-4137).

Human antibodies can be produced without prior immunization by displaying very large and diverse V-gene repertoires on phage (Marks et al. (1991) *J. Mol. Biol.* 222: 581-597). In one embodiment natural $V_H$ and $V_L$ repertoires present in human peripheral blood lymphocytes were isolated from unimmunized donors by PCR. The V-gene repertoires were spliced together at random using PCR to create a scFv gene repertoire which was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581-597; Marks et al. (1993). *Bio/Technology.* 10: 779-783; Griffiths et al. (1993) *EMBO J.* 12: 725-734; Clackson et al. (1991) *Nature.* 352: 624-628). Antibodies have been produced against self proteins, including human thyroglobulin, immunoglobulin, tumor necrosis factor and CEA (Griffiths et al. (1993) *EMBO J.* 12: 725-734). It is also possible to isolate antibodies against cell surface antigens by selecting directly on intact cells. For example, antibody fragments against four different erythrocyte cell surface antigens were produced by selecting directly on erythrocytes (Marks et al. (1993). *Bio/Technology.* 10: 779-783). Antibodies were produced against blood group antigens with surface densities as low as 5,000 sites/cell. The antibody fragments were highly specific to the antigen used for selection, and were functional in agglutination and immunofluorescence assays. Antibodies against the lower density antigens were produced by first selecting the phage antibody library on a highly related cell type which lacked the antigen of interest. This negative selection removed binders against the higher density antigens and subsequent selection of the depleted phage antibody library on cells expressing the antigen of interest resulted in isolation of antibodies against that antigen. With a library of this size and diversity, at least one to several binders can be isolated against a protein antigen 70% of the time. The antibody fragments are highly specific for the antigen used for selection and have affinities in the 1 μM to 100 nM range (Marks et al. (1991) *J. Mol. Biol.* 222: 581-597; Griffiths et al. (1993) *EMBO J.* 12: 725-734). Larger phage antibody libraries result in the isolation of more antibodies of higher binding affinity to a greater proportion of antigens.

The creation of a suitable large phage display antibody library is described in detail in the examples provided herein.

2) Phage Display can be Used to Increase Antibody Affinity.

To create higher affinity antibodies, mutant antibody gene repertoires, based on the sequence of a binding F5 or C1 antibody (e.g., based on the scFv F5 or C1 antibodies described herein), are created and expressed on the surface of phage. Higher affinity scFvs are selected on antigen as described above, in the Examples, and in Schier et al. (1996) *j. Mol. Biol.,* 263: 551-567.

Higher affinity scFvs are selected by affinity chromatography on antigen as described above. One approach to creating mutant scFv gene repertoires has been to replace the original $V_H$ or $V_L$ gene with a repertoire of V-genes to create new partners (chain shuffling) (Clackson et al. (1991) *Nature.* 352: 624-628). Using chain shuffling and phage display, the affinity of a human scFv antibody fragment which bound the hapten phenyloxazolone (phOx) was increased from 300 nM to 1 nM (300 fold) (Marks et al. (1992) *Bio/Technology* 10: 779-783).

Thus, for example, to alter the affinity of F5 or C1 antibodies, a mutant scFv gene repertoire can be created containing the $V_H$ gene of F5 or C1 and a human $V_L$ gene repertoire (light chain shuffling). The scFv gene repertoire can be cloned into the phage display vector pHEN-1 (Hoogenboom et al. (1991) *Nucleic Acids Res.,* 19: 4133-4137) and after transformation a library of transformants is obtained. Phage are prepared and concentrated as described in the Examples.

Similarly, for heavy chain shuffling, the F5 or C1 $V_H$ CDR1 and/or CDR2, and/or CDR3 and light chain are cloned into a vector containing a human $V_H$ gene repertoire to create a phage antibody library transformants. For detailed descriptions of chain shuffling to increase antibody affinity see Schier et al. (1996) *J. Mol. Biol.,* 255: 28-43, 1996.

C1 and F5 selections can be performed by incubating the phage with biotinylated c-erbB-2 in solution. The antigen concentration is decreased each round, reaching a concentration less than the desired $K_d$ by the final rounds of selection. This results in the selection of phage on the basis of affinity (Hawkins et al. (1992) *J. Mol. Biol.* 226: 889-896).

3) Site-Directed Mutagenesis to Improve Binding Affinity.

The majority of antigen contacting amino acid side chains are located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.,* 196: 901-917; Chothia et al. (1986) *Science,* 233: 755-8; Nhan et al. (1991) *J. Mol. Biol.,* 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Site-directed mutagenesis of CDRs and screening against c-erbB-2 may be used to generate C6 antibodies having improved binding affinity and/or internalization of F5 and C1 antibodies.

4) CDR Randomization to Produce Higher Affinity Human scFv.

In an extension of simple site-directed mutagenesis, mutant antibody libraries can be created where partial or entire CDRs are randomized ($V_L$ CDR1 and CDR2 and $V_H$ CDR1, CDR2 and CDR3). In one embodiment, each CDR is randomized in a separate library, using F5 or C1 as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.,* 234: 564-578).

$V_H$ CDR3 occupies the center of the binding pocket, and thus mutations in this region are likely to result in an increase in affinity (Clackson et al. (1995) *Science,* 267: 383-386). In one embodiment, four $V_H$ CDR3 residues are randomized at a time using the nucleotides NNS (see, e.g., Schier et al. (1996) *Gene,* 169: 147-155; Schier and Marks (1996) *Human Antibodies and Hybridomas.* 7: 97-105, 1996; and Schier et al. (1996) *J. Mol. Biol.* 263: 551-567, 1996).

To create the library, an oligonucleotide is synthesized which anneals to the F5 or C1 $V_H$ framework 3 and encodes $V_H$ CDR3 and a portion of framework 4. At the four positions to be randomized, the sequence NNS is used, where N=any of the 4 nucleotides, and S=C or T. The oligonucleotides are used to amplify the F5 or C1 $V_H$ genes using PCR, creating a mutant F5 or C1 $V_H$ gene repertoire. PCR is used to splice the $V_H$ gene repertoire with the C6NIL3-B1 light chain gene, and the resulting scFv gene repertoire cloned into the phage display vector pHEN-1. Ligated vector DNA is used to transform electrocompetent *E. coli* to produce a phage antibody library of >1.0×10$^7$ clones (Id.).

To select higher affinity mutant scFv, each round of selection of the phage antibody libraries is conducted on decreasing amounts of biotinylated c-erbB-2, as described above. Typically, 96 clones from the third and fourth round of selection are screened for binding to c-erbB-2 by ELISA on 96 well plates. scFv from twenty to forty ELISA positive clones are expressed in 10 ml cultures, the periplasm harvested, and the scFv $k_{off}$ determined by BIAcore. Clones with the slowest $k_{off}$ are sequenced, and each unique scFv subcloned, e.g., into pUC119 Sf-NotmycHis. scFv is expressed in 1 L cultures, and purified as described supra. Affinities of purified scFv are determined by BIAcore.

5) Creation of Homodimers.

To create F5 or C1 (scFv')$_2$ antibodies, two F5 or two C1 scFvs are joined, either through a linker (e.g., a carbon linker, a peptide, etc.) or through a disulfide bond between, for example, two cysteines. Thus, for example, to create disulfide linked F5 scFv, a cysteine residue is introduced by site directed mutagenesis between the myc tag and hexahistidine tag at the carboxy-terminus of F5. Introduction of the correct sequence can be verified by DNA sequencing. If the construct is in pUC119, the pelB leader directs expressed scFv to the periplasm and cloning sites (Nco1 and Not1) exist to introduce F5 or C1 mutant scFv. The expressed scFv has the myc tag at the C-terminus, followed by 2 glycines, a cysteine, and then 6 histidines to facilitate purification by IMAC. After disulfide bond formation between the two cysteine residues, the two scFv are separated from each other by about 26 amino acids (two 11 amino acid myc tags and 4 glycines).

An scFv can be expressed from this construct, purified by IMAC, and analyzed by gel filtration. To produce (scFv')2 dimers, the cysteine is reduced by incubation with 1 mM β-mercaptoethanol, and half of the scFv blocked by the addition of DTNB. Blocked and unblocked scFvs are incubated together to form (scFv')2 and the resulting material can be analyzed by gel filtration. The affinity of the F5 and C1 scFv' monomers and the F5 and C1 (scFv')2 dimers is determined by BIAcore.

In a particularly preferred embodiment, the (scFv')$_2$ dimer is created by joining the scFv' fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

B) Recognizing/Selecting F5 or C1 Antibodies

As indicated above, in one embodiment, this invention provides two anti-c-erbB-2 antibodies that are effectively internalized. These antibodies, designated herein as F5 (SEQ ID NO: 1) and C1 (SEQ ID NO: 2), specifically bind to a previously unrecognized epitope on the external domain of c-erB-2, and thereby characterize that epitope. Using the information provided, other F5 and C1 antibodies that bind the same epitope can be routinely prepared.

Regardless of the method used to generate new C1 or F5 antibodies (e.g. animal immunization with c-erbB2, domain shuffling in a single-chain antibody library, etc.) to verify that the antibody produced is a preferred F5 or C1 antibody, the putative F5 or C1 antibody is preferably screened for 1) binding affinity for c-erbB2; and/or 2) specific binding of the F5 and/or C1 epitope; and 3) internalization.

1) Measurement of antibody/polypeptide binding affinity.

As explained above, selection for increased avidity involves measuring the affinity of the antibody (e.g. a modified F5 or C1) for the target antigen (e.g., c-erbB-2). Methods of making such measurements are described in detail in application U.S. Ser. No. 08/665,202, now U.S. Pat. No. 5,977, 322. Briefly, for example, the $K_d$ of F5- or C1-derived antibody the kinetics of binding to c-erbB-2 are determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant Kd is often calculated as $k_{off}/k_{on}$ and thus is typically measured in the range $10^{-5}$ to $10^{-12}$. Affinities measured in this manner correlate well with affinities measured in solution by fluorescence quench titration.

Preferred F5 and C1 antibodies bind to the c-erbB-2 F5 and C1 epitope on cells with a binding affinity of at least $10^{-5}$M, more preferably with a binding affinity of at least 1 µM, and most preferably with a binding affinity of at least 100 nM, 10 nM, or even 1 nM.

2) Identification of Antibodies that Bind the Epitope Bound by F5 and/or C1

The F5 and C1 antibodies (e.g., antibodies that bind the same epitope bound by C1 and F5) can be identified (selected) from serum derived from an appropriately immunized animal, or from an ex vivo system (e.g., a random antibody library) by selection for antibodies that compete with C1 or F5 for binding to a c-erbB2 epitope. The F5 and C1 derived antibodies are recognized by their cross-reactivity with either 1) the c-erbB-2 epitope recognized by F5 and C1; and/or 2) an anti F5 or C1 idiotypic antibody. For targeting and internalization, high affinity F5 and C1 antibodies are preferred, however, if it is desired to convert an antagonist to an agonist it is expected that low affinity F5 and C1 antibodies may be preferred. Moreover, for many applications rapid and efficient internalization is more important than affinity and a lower affinity antibody that is rapidly internalized may be preferred to a higher affinity antibody that is not internalized as quickly.

a) Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

F5- and C1-derived antibodies can then be recognized by their ability to specifically bind to F5 and C1-anti-idiotypic antibodies, i.e., F5- and C1-derived antibodies are preferably cross-reactive with F5 and C1 with F5 or C1 anti-idiotypic antibodies.

Anti-idiotypic antibodies can be raised against the variable regions of F5 or C1 using standard methods well known to those of skill in the art. Briefly, anti-idiotype antibodies can be made by injecting antibodies of this invention (e.g. F5 or C1 antibodies or fragments thereof (e.g., CDRs)) into an animal thereby eliciting antiserum against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line that does not secrete an immunoglobulin. Several such lines are known in the art. A preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures which remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

b) Cross-Reactivity with F5 or C1.

Instead of the anti-idiotypic antibody, putative F5- and C1-derived antibodies can be identified by cross-reactivity with F5 and C1, respectively, against the c-erbB-2 F5 and C1 epitopes.

This can be ascertained by providing cells expressing native or recombinant c-erbB-2 or by providing the isolated c-erbB-2 attached to a solid support. Competition between the putative F5 (or C1) and the F5 or C1 of SEQ ID NOS: 1 and 2, respectively, in an epitope-mapping format establishes that the antibodies are competing for the same epitope. The putative antibodies are then screened as described below.

c) Cross-Reactivity Measurements.

Immunoassays in the competitive binding format are preferably used for crossreactivity determinations. For example, the F5 or C1 epitope or anti-idiotypic antibody is immobilized to a solid support. The putative F5-derived or C1-derived antibodies (e.g. generated by selection from a phage-display library) added to the assay compete with F5 or C1 antibodies of SEQ ID NOS 1 and 2, respectively binding to the immobilized epitope or anti-idiotypic antibody. The ability of the putative F5-derived or C1-derived antibodies to compete with the binding of the F5 or C1 antibodies (SEQ ID NOS: 1 and 2) to the immobilized protein are compared. The percent crossreactivity above proteins is calculated, using standard calculations.

If the putative F5-derived or C1-derived antibody competes with F5 or C1 and has a binding affinity comparable to or greater than F5 or C1 with the same target then the putative F5-derived or C1-derived antibody is regarded as an F5 or C1 (derived) antibody.

3) Measurement of C1 and F5 Antibody Internalization.

In one embodiment, this invention provides methods for identifying internalizing F5 or C1 antibodies. The methods involve contacting a "target" cell with one or more putative F5 or C1 antibodies (e.g. members of a phage display library). After a suitable incubation period, the cells are washed to remove externally bound phage (library members) and then internalized phage are released from the cells by cell lysis. The internalized phage in the cell lysate can be recovered and expanded by using the lysate containing internalized phage to infect a bacterial host. Growth of infected bacteria leads to expansion of the phage that can be used for a subsequent round of selection. Each round of selection enriches for phage that are more efficiently internalized, more specific for the target cell or have improved binding characteristics.

The phage display library is preferably contacted with a subtractive cell line (i.e. a subtractive cell line is added to the target cells and culture media) to remove members of the phage display library that are not specific to the "target" cell(s). The subtractive cell line is preferably added under conditions in which members of the phage display library are not internalized (e.g., at a temperature of about 4° C. to about 20° C., more preferably at a temperature of about 4° C.) so that non-specific binding members of the library are not internalized (sequestered) before they can be subtracted out by the subtractive cell line.

After subtracting out non-specific binding antibodies, the "target" cells are washed to remove the subtractive cell line and to remove non-specifically or weakly-bound phage."

The target cells are then cultured under conditions where it is possible for internalization to occur (e.g. at a temperature of about 35° C. to about 39° C., more preferably at a temperature of about 37° C.). The duration of the internalization culture period will determine the internalization speed of the antibodies (phage display members) for which selection takes place. With shorter internalization periods more rapid internalizing antibodies are selected while with longer internalization periods slower internalizing antibodies are selected. The internalization period is preferably less than about 120 minutes, more preferably less than about 60 minutes, and most preferably less than about 30 minutes or even less than about 20 minutes.

It is noted that during the internalization period the target cells are grown under conditions in which internalization can occur. For a number of cell lines, this involves culturing the cells adherently on culture plates.

After internalization has been allowed to occur the target cells are washed to remove non-internalized (e.g. surface-bound phage).

The cells can then be moved to clean media. In a preferred embodiment, where the cells are adherent, they cells are trypsinized to free the cells from the extracellular matrix which may contain phage antibodies that bind the extracellular matrix. Freeing the cells into solution permits more through washing and moving of the cells to a new culture flask will leave behind any phage that may have stuck to the tissue culture dish.

The cells can then be washed with a large volume of PBS and lysed to release the internalized phage which can then be expanded e.g. used to infect *E. coli* to produce phage for the next round of selection. It is noted that there is no need to actually visualize the internalized phage. Simple cell lysis and expansion of the formerly internalized phage is sufficient for recovering internalizing phage display members. Methods of selecting for internalizing phage library members are also described in related application U.S. Ser. No. 60/082,953 and in the Examples provided herein.

IV. F5 and C1 Epitopes

In another embodiment, this invention provides for the epitope(s) specifically recognized and bound by the F5 and C1 antibodies of this invention. This internalizing epitope is characterized by the ability to be specifically bound by F5 and C1 respectively. Thus, the F5 epitope is a region of c-erbB2 that specifically binds F5 (SEQ ID NO: 1) while the C1 epitope is a region of c-erbB2 that specifically binds C1 (SEQ ID NO: 2). It is believed that F5 and C1 both bind to the same c-erbB2 epitope.

The F5 and C1 epitopes can identified by epitope mapping using standard techniques (see, e.g., Geysen et al (1987) *J. Immunol. Meth.* 102, 259-274). This technique involves the synthesis of overlapping c-erbB-2 peptides. The synthesized peptides are then screened against F5 and C1 respectively, and the characteristic F5 and C1 epitopes can be identified by binding specificity and affinity.

The peptides for F5 and C1 epitope mapping can be conveniently prepared using "Multipin" peptide synthesis techniques (see, e.g., Geysen et al (1987) *Science*, 235:1184-1190). Using the known sequence of c-erbB-2 (see, e.g., SWISS-PROT: P04626 or Coussens et al. (1985) *Science*, 230: 1132-1139), overlapping c-erbB-2 polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in PBS for 1 hour at room temperature. Then the pins are then inserted into the individual wells of 96-well microtest plate containing antibody F5 or C1 in the pre-coat buffer at 2 mu g/ml. The incubation is for 1 hour at room temperature. The pins are washed in PBST (3 rinses for every 10 minutes), and then incubated in the wells of a 96-well microtest plate containing 100 mu 1 of HRP-conjugated goat anti-mouse IgG (Fc) (Jackson ImmunoResearch Laboratories) at a 1:4,000 dilution for 1 hour at room temperature. After the pins are washed as before, the pins were put into wells containing peroxidase substrate solution of diammonium 2,2'-azino-bis [3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm Wells showing color development indicated reactivity of the c-erbB-2 derived peptides in such wells with F5 or C1.

V. Preparation of Chimeric Molecules

In another embodiment this invention provides for chimeric molecules comprising an F5 or C1 antibody attached to an effector molecule. As explained above, the effector molecule component of the chimeric molecules of this invention may be any molecule whose activity it is desired to deliver to cells that express c-erbB-2. Suitable effector molecules include cytotoxins such as PE, Ricin, Abrin or DT, radionuclides, ligands such as growth factors, antibodies, detectable labels such as fluorescent or radioactive labels, and therapeutic compositions such directly fused or conjugated drugs, "capsules" (e.g. liposomes, synthetic polymer capsules, virus capsids, live virus) containing various drugs or other agents (e.g. nucleic acids).

An effector molecule typically has a characteristic activity that is desired to be delivered to the target cell (e.g. a tumor overexpressing c-erbB-2). Effector molecules include cytotoxins, labels, radionuclides, ligands, antibodies, drugs, liposomes, viruses or viral capsids containing nucleic acids ((e.g. DNA, RNA, antisense molecules, peptide nucleic acids, etc.), and viral coat proteins that render the virus capable of infecting a c-erbB-2 expressing cell. Once delivered to the target, the effector molecule exerts its characteristic activity.

For example, in one embodiment, where the effector molecule is a cytotoxin, the chimeric molecule acts as a potent cell-killing agent specifically targeting the cytotoxin to tumor cells bearing the c-erbB-2 marker. Chimeric cytotoxins that specifically target tumor cells are well known to those of skill in the art (see, e.g., Pastan et al. (1992) *Ann. Rev. Biochem.*, 61: 331-354).

In another embodiment, the chimeric molecule may be used for detecting the presence or absence of tumor cells in vivo or in vitro, and/or for quantifying tumor cells in vivo or in vitro, and/or for localizing tumor cells in vivo. These methods involve providing a chimeric molecule comprising an effector molecule, that is a detectable label attached to the F5 or C1 antibody. The F5 or C1 antibodies specifically bind the chimeric molecule to tumor cells expressing the c-erbB-2 marker which are then marked by their association with the detectable label. Subsequent detection of the cell-associated label indicates the presence and/or location of a tumor cell.

In yet another embodiment, the effector molecule may be another specific binding moiety including, but not limited to an antibody, an antigen binding domain, a growth factor, or a ligand. The chimeric molecule will then act as a highly specific bifunctional linker. This linker may act to bind and enhance the interaction between cells or cellular components to which the chimeric protein binds. Thus, for example, where the "effector" component is an anti-receptor antibody or antibody fragment, the F5 or C1 antibody component specifically binds c-erbB-2 bearing cancer cells, while the effector component binds receptors (e.g., IL-2, IL-4, FcI, FcII and FcIII receptors) on the surface of immune cells. The chimeric molecule may thus act to enhance and direct an immune response toward target cancer cells.

In still yet another embodiment the effector molecule may be a pharmacological agent (e.g. a drug) or a vehicle containing a pharmacological agent. This is particularly suitable where it is merely desired to invoke a non-lethal biological response. Thus the F5 or C1 antibody receptor may be conjugated to a drug such as vinblastine, vindesine, melphalan, N-Acetylmelphalan, methotrexate, aminopterin, doxirubicin, daunorubicin, genistein (a tyrosine kinase inhibitor), an antisense molecule, and other pharmacological agents known to those of skill in the art, thereby specifically targeting the pharmacological agent to tumor cells expressing c-erbB-2.

Alternatively, the F5 or C1 antibody may be bound to a vehicle containing the therapeutic composition. Such vehicles include, but are not limited to liposomes, micelles, various synthetic beads or polymer capsules, virus capsids, live virus, and the like.

One of skill in the art will appreciate that the chimeric molecules of the present invention optionally includes multiple targeting moieties bound to a single effector or conversely, multiple effector molecules bound to a single targeting moiety. In still other embodiment, the chimeric molecules includes both multiple targeting moieties and multiple effector molecules. Thus, for example, this invention provides for "dual targeted" cytotoxic chimeric molecules in which the F5 or C1 antibody is attached to a cytotoxic molecule while another molecule (e.g. an antibody, or another ligand) is attached to the other terminus of the toxin. Such a dual-targeted cytotoxin might comprise, e.g. an F5 or C1 antibody substituted for domain Ia at the amino terminus of a PE and anti-TAC(Fv) inserted in domain III. Other antibodies may also be suitable effector molecules.

A) Cytotoxins.

Particularly preferred cytotoxins include *Pseudomonas* exotoxins, *Diphtheria* toxins, ricin, and abrin. *Pseudomonas* exotoxin and *Dipthteria* toxin, in particular, are frequently used in chimeric cytotoxins.

1) *Pseudomonas* Exotoxin (PE).

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO: 5) (as in native PE), RDEL (SEQ ID NO: 6), RDEL (SEQ ID NO: 7), or KDEL (SEQ ID NO: 8), repeats of those, or other sequences that function to maintain or recycle proteins into the endoplasmic reticulum, referred to here as "endoplasmic retention sequences". See, for example, Chaudhary et al. (1991)*Proc. Natl. Acad. Sci. USA* 87:308-312 and Seetharam et al (1991) *J. Biol. Chem.* 266: 17376-17381.

The targeting molecule can be inserted in replacement for domain Ia. A similar insertion has been accomplished in what is known as the TGF-PE40 molecule (also referred to as TP40) described in Heimbrook et al. (1990) *Proc. Natl. Acad. Sci.*, USA, 87: 4697-4701. See also, Debinski et al. (1994) *Bioconj. Chem.*, 5: 40, for other PE variants).

The PE molecules can be fused to the F5 or C1 antibody by recombinant means. The genes encoding protein chains may be cloned in cDNA or in genomic form by any cloning procedure known to those skilled in the art. See for example Sambrook et al., *Molecular Cloning: A Laboratory Manual*, Cold Spring Harbor Laboratory, (1989). Methods of cloning genes encoding PE fused to various ligands are well known to those of skill in the art. See, for example, Siegall et al. (1989) *FASEB J.*, 3: 2647-2652; Chaudhary et al. (1997) *Proc. Natl. Acad. Sci. USA*, 84: 4538-4542.

Those skilled in the art will realize that additional modifications, deletions, insertions and the like may be made to the chimeric molecules of the present invention or to the nucleic acid sequences encoding the F5 or C1 chimeric molecules. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

2) *Diphtheria* Toxin (DT).

Like PE, *diphtheria* toxin (DT) kills cells by ADP-ribosylating elongation factor 2 (EF-2) thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., (1972) *Science,* 175: 901-903; Uchida et al. (1973) *J. Biol. Chem.,* 248: 3838-3844).

The targeting molecule-*Diphtheria* toxin fusion proteins of this invention may have the native receptor-binding domain removed by truncation of the *Diphtheria* toxin B chain. DT388, a DT in which the carboxyl terminal sequence beginning at residue 389 is removed is illustrated in Chaudhary, et al. (1991) *Bioch. Biophys. Res. Comm.,* 180: 545-551.

Like the PE chimeric cytotoxins, the DT molecules may be chemically conjugated to the F5 or C1 antibody, but may also be prepared as fusion proteins by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. (1990) *J. Biol. Chem.* 265: 11885-11889 which describes the expression of growth-factor-DT fusion proteins.

The term "*Diphtheria* toxin" (DT) as used herein refers to full length native DT or to a DT that has been modified. Modifications typically include removal of the targeting domain in the B chain and, more specifically, involve truncations of the carboxyl region of the B chain.

B) Detectable Labels.

The term "detectable label" refers to any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), fluorescent proteins (e.g. green fluorescent protein (GFP), blue fluorescent protein (BFP), yellow fluorescent protein (YFP), red fluorescent protein (RFP), luciferase), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

The label may be coupled directly or indirectly to the desired component of the assay according to methods well known in the art. Non radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly or thorough a linker to signal generating compounds.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C) Ligands.

As explained above, the effector molecule may also be a ligand or an antibody. Particularly preferred ligand and antibodies are those that bind to surface markers of immune cells. Chimeric molecules utilizing such antibodies as effector molecules act as bifunctional linkers establishing an association between the immune cells bearing binding partner for the ligand or antibody and the tumor cells expressing the c-erbB-2. Suitable antibodies and growth factors are known to those of skill in the art and include, but are not limited to, IL-2, IL-4, IL-6, IL-7, tumor necrosis factor (TNF), anti-Tac, TGFβ, and the like.

D) Other Therapeutic Moieties.

Other suitable effector molecules include pharmacological agents or encapsulation systems containing various pharmacological agents. Thus, the F5 or C1 antibody may be attached directly to a drug that is to be delivered directly to the tumor. Such drugs are well known to those of skill in the art and include, but are not limited to, doxirubicin, vinblastine, genistein, antisense molecules, ribozymes and the like.

Alternatively, the effector molecule may comprise an encapsulation system, such as a liposome, polymer capsule, viral capsid, virus, or micelle that contains a therapeutic composition such as a drug, a nucleic acid (e.g. an antisense nucleic acid including, but not limited to a protein nucleic acid), or another therapeutic moiety that is preferably shielded from direct exposure to the circulatory system. Means of preparing liposomes attached to antibodies are well known to those of skill in the art. See, for example, U.S. Pat. No. 4,957,735 and Connor et al. (1985) *Pharm. Ther.,* 28: 341-365.

In a particularly preferred embodiment, the liposome is a "stealth" (sterically stabilized) liposome bearing an external hydrophilic polymer (e.g. polyethylene glycol (PEG). The antibody can be coupled to the liposome through the hydrophilic polymer as described in application U.S. Ser. No. 08/665,202, now U.S. Pat. No. 5,977,322.

E) Attachment of the F5 or C1 Antibody to the Effector Molecule.

One of skill will appreciate that the F5 or C1 antibody and the effector molecule may be joined together in any order. Thus the effector molecule may be joined to either the amino or carboxy termini of the F5 or C1 antibody. The F5 or C1 antibody may also be joined to an internal region of the effector molecule, or conversely, the effector molecule may be joined to an internal location of the F5 or C1 antibody as long as the attachment does not interfere with the respective activities of the molecules.

The F5 or C1 antibody and the effector molecule may be attached by any of a number of means well known to those of skill in the art. Typically the effector molecule is conjugated, either directly or through a linker (spacer), to the F5 or C1 antibody. However, where the effector molecule is a polypeptide it is preferable to recombinantly express the chimeric molecule as a single-chain fusion protein.

i) Conjugation of the Effector Molecule to the F5 or C1 Antibody.

In one embodiment, the targeting molecule F5 or C1 antibody is chemically conjugated to the effector molecule (e.g. a cytotoxin, a label, a ligand, or a drug or liposome). Means of chemically conjugating molecules are well known to those of skill (see, for example, Chapter 4 in *Monoclonal Antibodies: Principles and Applications*, Birch and Lennox, eds. John Wiley & Sons, Inc. N.Y. (1995) which describes conjugation of antibodies to anticancer drugs, labels including radio labels, enzymes, and the like).

The procedure for attaching an agent to an antibody or other polypeptide targeting molecule will vary according to the chemical structure of the agent. Polypeptides typically contain variety of functional groups; e.g., carboxylic acid (COOH) or free amine ($—NH_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of a sugar moiety attached to the protein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071-4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann, *Science*, 252: 1657 (1991), U.S. Pat. Nos. 4,545,985 and 4,894,443.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers that are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

ii) Production of Fusion Proteins.

Where the F5 or C1 antibody and/or the effector molecules are relatively short (i.e., less than about 50 amino acids) they may be synthesized using standard chemical peptide synthesis techniques. Where both molecules are relatively short the chimeric molecule may be synthesized as a single contiguous polypeptide. Alternatively the F5 or C1 antibodies and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology*. Vol. 2: *Special Methods in Peptide Synthesis, Part A.*, Merrifield, et al. *J. Am. Chem. Soc.*, 85: 2149-2156 (1963), and Stewart et al., *Solid Phase Peptide Synthesis*, 2nd ed. Pierce Chem. Co., Rockford, Ill. (1984).

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. F5 or C1 Ab-PE) of this invention may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, for example, the gene for the F5 or C1 antibody may be amplified from a nucleic acid template (clone) using a sense primer containing a first restriction site and an antisense primer containing a second restriction site. This produces a nucleic acid encoding the mature F5 or C1 antibody sequence and having terminal restriction sites. A cytotoxin (or other polypeptide effector) may be cut out of a plasmid encoding that effector using restriction enzymes to produce cut ends suitable for annealing to the F5 or C1 antibody. Ligation of the sequences and introduction of the construct into a vector produces a vector encoding the F5- or C1-effector molecule fusion protein. Such PCR cloning methods are well known to those of skill in the art (see, for example, Debinski et al. (1994) Int. J. Cancer, 58: 744-748, for an example of the preparation of a PE fusion protein).

While the two molecules may be directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity. One of skill will appreciate that PCR primers may be selected to introduce an amino acid linker or spacer between the F5 or C1 antibody and the effector molecule if desired.

The nucleic acid sequences encoding the fusion proteins may be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*., Academic Press, Inc. N.Y. (1990)). In a preferred embodiment, the fusion proteins are purified using affinity purification methods as described in Examples 1 and 2. Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the F5 or C1 antibody-effector fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art. (See, Debinski et al. *J. Biol. Chem.* (1993) 268: 14065-14070; Kreitman and Pastan (1993) *Bioconjug. Chem.*, 4: 581-585; and Buchner, et al. (1992) *Anal. Biochem.*, 205: 263-270. Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the F5 or C1 antibody-effector fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

VI. Diagnostic Assays

As explained above, the F5 or C1 antibodies may be used for the in vivo or in vitro detection and/or quantitation of c-erbB-2 and thus, in the diagnosis and/or localization of cancers characterized by the expression of c-erbB-2.

A) In Vivo Detection of c-erB-2.

The F5 and C1 antibodies and/or chimeric molecules of the present invention may be used for in vivo detection and localization of cells (e.g. c-erbB-2 positive carcinoma) bearing c-erbB-2. Such detection involves administering to an organism a chimeric molecule comprising a F5 or C6 antibody joined to a label detectable in vivo. Such labels are well known to those of skill in the art and include, but are not limited to, electron dense labels such as gold or barium which may be detected by X-ray or CAT scan, various radioactive labels that may be detected using scintillography, and various magnetic and paramagnetic materials that may be detected using positron emission tomography (PET) and magnetic resonance imaging (MRI). The F5 or C1 antibody associates the label with the c-erbB-2 bearing cell which is then detected and localized using the appropriate detection method.

B) In Vitro Detection of c-erB-2.

The F5 and C1 antibodies of this invention are also useful for the detection of c-erbB-2 in vitro e.g., in biological samples obtained from an organism. The detection and/or quantification of c-erbB-2 in such a sample is indicative the presence or absence or quantity of cells (e.g., tumor cells) overexpressing c-erbB-2.

The c-erbB-2 antigen may be quantified in a biological sample derived from a patient such as a cell, or a tissue sample derived from a patient. As used herein, a biological sample is a sample of biological tissue or fluid that contains a c-erbB-2 antigen concentration that may be correlated with and indicative of cells overexpressing c-erbB-2. Preferred biological samples include blood, urine, and tissue biopsies.

In a particularly preferred embodiment, erB-2 is quantified in breast tissue cells derived from normal or malignant breast tissue samples. Although the sample is typically taken from a human patient, the assays can be used to detect erB-2 in cells from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

C) Assay Formats (Detection or Quantification of c-erbB-2).

1) Immunological Binding Assays

The c-erB-2 peptide (analyte) or an anti-c-erb-2 antibody is preferably detected in an immunoassay utilizing a F5 or C1 antibody as a capture agent that specifically binds to a c-erbB-2 peptide.

As used herein, an immunoassay is an assay that utilizes an antibody (e.g. a F5 or C1 antibody) to specifically bind an analyte (e.g., c-erb-2). The immunoassay is characterized by the use of specific binding to a F5 or C1 antibody as opposed to other physical or chemical properties to isolate, target, and quantify the c-erB-2 analyte.

The c-erbB-2 marker may be detected and quantified using any of a number of well recognized immunological binding assays. (See for example, U.S. Pat. Nos. 4,366,241; 4,376,110; 4,517,288; and 4,837,168) For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991)).

The immunoassays of the present invention are performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY.

Immunoassays often utilize a labeling agent to specifically bind to and label the binding complex formed by the capture agent and the analyte (i.e., a F5 or C1 antibody-erB-2 complex). The labeling agent may itself be one of the moieties comprising the antibody/analyte complex. Thus, the labeling agent may be a labeled c-erB-2 peptide or a labeled F5 or C1 antibody. Alternatively, the labeling agent is optionally a third moiety, such as another antibody, that specifically binds to the F5 or C1 antibody, the c-erB-2 peptide, the anti-c-erB-2 antibody/c-erB-2 peptide complex, or to a modified capture group (e.g., biotin) which is covalently linked to c-erB-2 or the F5 or C1 antibody.

In one embodiment, the labeling agent is an antibody that specifically binds to the F5 or C1 antibody. Such agents are well known to those of skill in the art, and most typically comprise labeled antibodies that specifically bind antibodies of the particular animal species from which the F5 or C1 antibody is derived (e.g., an anti-species antibody). Thus, for example, where the capture agent is a human derived F5 or C1 antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non immunogenic reactivity with immunoglobulin constant regions from a variety of species. See, generally Kronval, et al., (1973) *J. Immunol.*, 111: 1401-1406, and Akerstrom, et al., (1985) *J. Immunol.*, 135: 2589-2542.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays are carried out at ambient temperature, although they can be conducted over a range of temperatures, such as 5° C. to 45° C.

a) Non Competitive Assay Formats.

Immunoassays for detecting c-erb-2 are typically either competitive or noncompetitive. Noncompetitive immunoassays are assays in which the amount of captured analyte (in this case, c-erb-2) is directly measured. In one preferred "sandwich" assay, for example, the capture agent (e.g., F5 or C1 antibody) is bound directly or indirectly to a solid substrate where it is immobilized. These immobilized F5 or C1 antibodies capture c-erb-2 present in a test sample (e.g., a biological sample derived from breast tumor tissue). The c-erb-2 thus immobilized is then bound by a labeling agent, such as a second c-erb-2 antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive). One of skill will appreciate that the analyte and capture agent is optionally reversed in the above assay, e.g., when the presence, quantity or avidity of a F5 or C1 antibody in a sample is to be measured by its binding to an immobilized c-erb-2 peptide.

b) Competitive Assay Formats.

In competitive assays, the amount of analyte (e.g., c-erB-2) present in the sample is measured indirectly by measuring the amount of an added (exogenous) analyte displaced (or competed away) from a capture agent (e.g., F5 or C1 antibody) by the analyte present in the sample. In one competitive assay, a known amount of c-erb-2 is added to a test sample with an unquantified amount of c-erB-2, and the sample is contacted with a capture agent, e.g., a F5 or C1 antibody that specifically binds c-erb-2. The amount of added c-erB-2 which binds to the F5 or C1 antibody is inversely proportional to the concentration of c-erB-2 present in the test sample.

The F5 or C1 antibody can be immobilized on a solid substrate. The amount of erB-2 bound to the F5 or C1 antibody is determined either by measuring the amount of erB-2 present in an erB-2-C6 antibody complex, or alternatively by measuring the amount of remaining uncomplexed erB-2. Similarly, in certain embodiments where the amount of erB-2 in a sample is known, and the amount or avidity of a F5 or C1 antibody in a sample is to be determined, erB-2 becomes the capture agent (e.g., is fixed to a solid substrate) and the F5 or C1 antibody becomes the analyte.

c) Reduction of Non Specific Binding.

One of skill will appreciate that it is often desirable to reduce non specific binding in immunoassays and during analyte purification. Where the assay involves c-erB-2, F5 or C1 antibody, or other capture agent immobilized on a solid substrate, it is desirable to minimize the amount of non specific binding to the substrate. Means of reducing such non specific binding are well known to those of skill in the art. Typically, this involves coating the substrate with a proteinaceous composition. In particular, protein compositions such as bovine serum albumin (BSA), nonfat powdered milk, and gelatin are widely used.

d) Substrates.

As mentioned above, depending upon the assay, various components, including the erB-2, F5 or C1 or antibodies to erB-2 or F5 or C1, are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, *J. Biol. Chem.* 245 3059 (1970).

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

2) Other Assay Formats

C-erB-2 polypeptides or F5 or C1 antibodies and can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of erB-2 peptides and F5 or C1 antibodies in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the erB-2 peptide or the anti-erB-2 antibody. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds either anti-erB-2 or erB-2 as appropriate.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

VII. Pharmaceutical Compositions

The F5 and C1 antibodies and chimeric molecules of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, typically a c-erbB-2 positive carcinoma, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One application is the treatment of cancer, such as by the use of a F5 or C1 antibody attached to a cytotoxin.

Another approach involves using a ligand that binds a cell surface marker (receptor) so the chimeric associates cells bearing the ligand substrate are associated with the c-erbB-2 overexpressing tumor cell. The ligand portion of the molecule is chosen according to the intended use. Proteins on the membranes of T cells that may serve as targets for the ligand includes FcI, FcII and FcIII, CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte target molecules for the chimeric molecules bearing a ligand effector are described in *Leukocyte Typing III*, A. J. McMichael, ed., Oxford University Press (1987). Those skilled in the art will realize ligand effectors may be chosen that bind to receptors expressed on still other types of cells as described above, for example, membrane glycoproteins or ligand or hormone receptors such as epidermal growth factor receptor and the like.

VIII. Kits for Diagnosis or Treatment

In another embodiment, this invention provides for kits for the treatment of tumors or for the detection of cells overexpressing c-erbB-2. Kits will typically comprise a chimeric molecule of the present invention (e.g. F5 and/or C1 antibody-label, F5 and/or C1 antibody-cytotoxin, F5 and/or C1 antibody-ligand, etc.). In addition the kits may optionally include instructional materials containing directions (i.e., protocols) disclosing means of use of the chimeric molecule(s) (e.g. as a cytotoxin, for detection of tumor cells, to augment an immune response, etc.). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti-human antibodies, or the like). The kits may additionally include buffers and other reagents routinely used for the practice of a particular method. Such kits and appropriate contents are well known to those of skill in the art.

EXAMPLES

The following examples are offered to illustrate, but not to limit the claimed invention.

Example 1

Creation of a Non-Immune Human Fab Phage Antibody Library Containing $10^9$-$10^{11}$ Members Manipulation of previous $10^7$ member phage display libraries revealed two major limitations: 1) expression levels of Fabs was too low to produce adequate material for characterization, and 2) the library was relatively unstable. These limitations are a result of creating the library in a phage vector, and the use of the cre-lox recombination system. We therefore decided that the best approach for this project was to create a very large scFv library using a phagemid vector. The goal was to produce a library at least 100 times larger than our previous $3.0 \times 10^7$ member scFv library. The approach taken was to clone the $V_H$ and $V_L$ library on separate replicons, combine them into an scFv gene repertoire by splicing by overlap extension, and clone the scFv gene repertoire into the phage display vector pHEN1. Human peripheral blood lymphocyte and spleen RNA was primed with IgM heavy chain constant region and, kappa and lambda light chain constant region primers and first strand cDNA synthesized. 1st strand cDNA was used as a template for PCR amplification of VH Vκk and Vλ, gene repertoires.

The $V_H$ gene repertoires were cloned into the vector pUC119Sfi-Not as NcoI-NotI fragments, to create a library of $8.0 \times 10^8$ members. The library was diverse by PCR fingerprinting. Single chain linker DNA was spliced onto the $V_L$ gene repertoires using PCR and the repertoire cloned as an XhoI-NotI fragment into the vector pHENIXscFv to create a library of $7.2 \times 10^6$ members. The $V_H$ and $V_L$ gene repertoires were amplified from their respective vectors and spliced together using PCR to create an scFv gene repertoire. The scFv gene repertoire was cloned as an NcoI-NotI fragment into the vector to create an scFv phage antibody library of $7.0 \times 10^9$ members. The library was diverse as determined by BstN1 fingerprinting.

To verify the quality of the library, phage were prepared and selected on 14 different protein antigens. The results are shown in Table 1. scFv antibodies were obtained against all antigens used for selection, with between 3 and

TABLE 1

Results of phage antibody library selections. For each antigen (column 1), the number and the percentage of positive clones selected (column 2) and the number of different antibodies isolated (column 3) is indicated

| Protein antigen used for selection | Percentage (number) of ELISA positive clones | Number of different antibodies isolated |
|---|---|---|
| FGF Receptor ECD | 69 (18/26) | 15 |
| BMP Receptor Type I ECD | 50 (12/24) | 12 |
| Activin Receptor Type I ECD | 66 (16/24) | 7 |
| Activin Receptor Type II ECD | 66 (16/24) | 4 |
| Erb-B2 ECD | 91 (31/34) | 14 |
| VEGF | 50 (48/96) | 6 |
| BoNT/A | 28 (26/92) | 14 |
| BoNT-A C-fragment | 95 (87/92) | 10 |
| BoNT/B | 10 (9/92) | 5 |
| BoNT/C | 12 (11/92) | 5 |
| BoNT/E | 9 (8/92) | 3 |
| Bungarotoxin | 67 (64/96) | 15 |
| Cytochrome b5 | 55 (53/96) | 5 |
| Chlamydia trachomatis EB | 66 (63/96) | 7 |

TABLE 2

Affinities and binding kinetics of anti-BoNT A C-fragment and anti-Erb-B2 scFv. Association ($k_{on}$) and dissociation ($k_{off}$) rate constants for purified scFvs were measured using surface plasmon resonance (BIAcore) and $K_d$ calculated as ($k_{off}/k_{on}$).

| Specificity and clone | $K_d$ ($\times 10^{-9}$ M) | $k_{on}$ ($\times 10^5$ M$^{-1}$s$^{-1}$) | $k_{off}$ ($\times 10^{-3}$ s$^{-1}$) |
|---|---|---|---|
| ErbB-2 B7A | 0.22 | 4.42 | 0.1 |
| ErbB-2 G11D | 0.48 | 2.19 | 0.11 |
| ErbB-2 A11A | 0.49 | 3.69 | 0.18 |
| ErbB-2 F5A | 4.03 | 1.62 | 0.65 |
| BoNT-A 2A9 | 26.1 | 0.25 | 0.66 |
| BoNT-A 2H6 | 38.6 | 2.2 | 8.5 |
| BoNT-A 3F6 | 66.0 | 4.7 | 30.9 |
| BoNT-A 2B6 | 71.5 | 1.1 | 7.8 |

For example, selection on *Chlamydia trachomatis* elementary bodies (the causative organism of Chlamydial disease) yielded seven that specifically recognized *chlamydia* (Table 1 and FIG. 3). The scFv could be successfully used in a number of immunologic assays including ELISA, immunofluorescence, Western blotting, epitope mapping and immunoprecipitation. The number of binding antibodies for each antigen, and the affinities of the binding scFv are comparable to results obtained from the best phage antibody libraries (Table 3). Thus the library was established as a source of panels of human antibodies against any antigen with affinities at least equivalent to the secondary murine response.

TABLE 3

Comparison of protein binding antibodies selected from non-immune phage-display antibody libraries.

| Library | Library size and type* | Number of protein antigens studied | Average number of antibodies per protein antigen | Number of affinities measured | Range of affinities for protein antigens $K_d$ ($\times 10^{-9}$ M) |
|---|---|---|---|---|---|
| Marks et al (1991) *J. Mol. Biol.* 222: 581-597 | $3.0 \times 10^7$ (scFv, N) | 2 | 2.5 | 1 | 100-2000 |
| Nissim et al (1994) *EMBO J.* 13: 692-698 | $1.0 \times 10^8$ (scFV, SS) | 15 | 2.6 | ND | ND |
| DeKruif et al (1995) *J. Mol. Biol.* 248: 97-105 | $3.6 \times 10^8$ (scFv, SS) | 12 | 1.9 | 3 | 100-2500 |
| Griffiths et al (1994) *EMBO J.* 13: 3245-3260 | $6.5 \times 10^{10}$ (Fab, SS) | 30 | 4.8 | 3 | 7-58 |
| Vaughan et al (1996) *Nature Biotechnology.* 14: 309-314 | $1.4 \times 10^{10}$ (scFv, N) | 3 | 7.0 | 3 | 4.2-8.0 |
| Present Examples | $6.7 \times 10^9$ (scFv, N) | 14 | 8.7 | 8 | 0.22-71.5 |

*For library type, N = V-gene repertoires obtained from V-genes rearranged in vivo; SS = semi-synthetic V-genes constructed from cloned V-gene segments and synthetic oligonucleotides encoding $V_H$ CDR3. ND = not determined.

Figure 2:
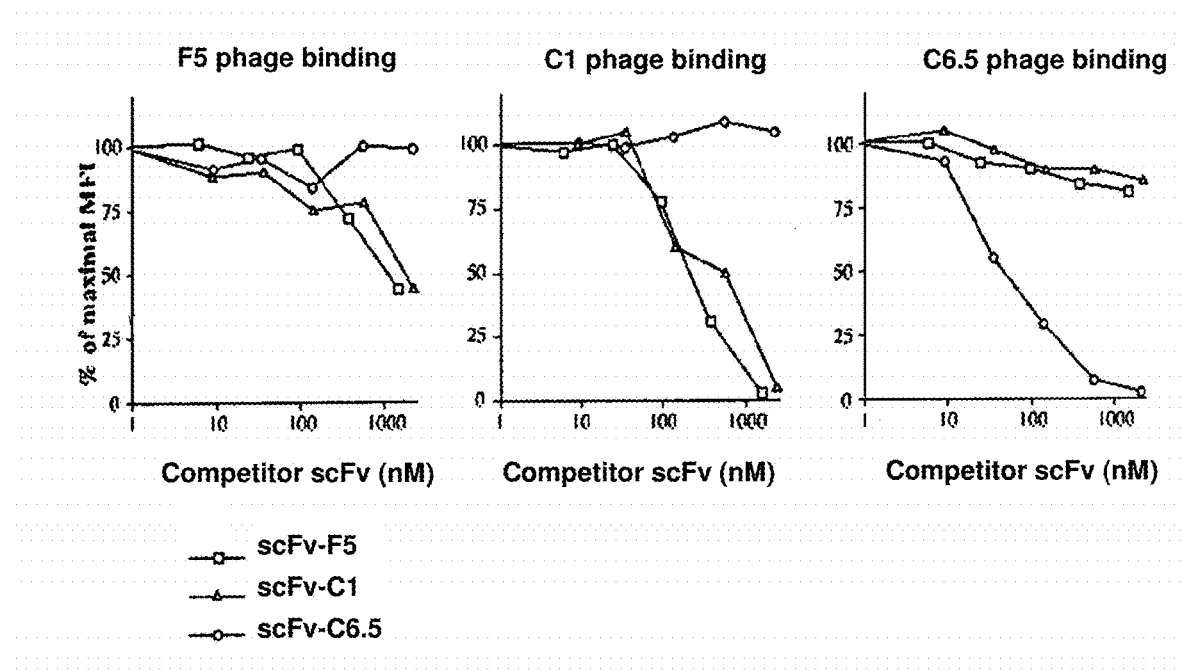
FIG. 2 illustrates epitope mapping of F5, C1 and C6.5 scFv Inhibition of binding of F5 phage (left panel), C1 phage (center panel) or C6.5 phage (right panel) by increasing concentrations of soluble scFv-F5 (o), scFv-C1 (Δ) or scFv-C6.5 (□). Bound phages were detected with an anti-M13 biotinylated Ab and streptavidin-PE. Results are expressed in % of maximal mean fluorescent intensity (MFI). Soluble F5 and C1 inhibited the binding of F5 or C1 phage, but not C6.5 phage.

15 unique scFv isolated per antigen (average 8.7) (Table 1). This compares favorably to results obtained from smaller scFv libraries (1 to a few binders obtained against only 70% of antigens used for selection). Affinities of 4 anti-ErbB-2 scFv and 4 anti-Botulinum scFv were measured using surface plasmon resonance in a BIAcore and found to range from $4.0 \times 10^{-9}$ M to $2.2 \times 10^{-10}$ M for the anti-ErbB2 scFv and $2.6 \times 10^{-8}$ M to $7.15 \times 10^{-8}$ M for the anti-Botulinum scFv (Table 2). scFv were highly specific for the antigen used for selection (FIG. 2). The library could also be successfully selected on complex mixtures of antigen.

These experiments demonstrate the creation of a high complexity human scFv phage antibody library from which a panel of high affinity human scFv can be generated against any purified antigen. Such a library is ideal for probing the surface of cells to identify novel cell surface markers.

Example 2

Uptake of scFV into Cells by Receptor Mediated Endocytosis and Subsequent Recovery The $7.0 \times 10^9$ member scFv phage antibody library described above was selected on the malignant breast tumor cell lines MB231 and ZR-75-1, both with and without negative selections on the normal breast cell line HBL100. Similar results were obtained as described in section above. scFv were isolated that could not distinguish malignant from non-malignant cell lines.

To increase the specificity of selections, it was hypothesized that phage binding cell surface receptors could be taken up into cells by receptor mediated endocytosis and could then be recovered from cells by lysing the cells. This assumed: 1) that phage could be internalized by receptor mediated endocytosis and 2) that phage could be recovered in the infectious state from within cells prior to lysosomal degradation. The ability to select for internalized phage antibodies would have two major benefits: 1) the identification of antibodies that bind to receptors capable of internalization and 2) an added level of specificity in the selection process. Identification of antibodies which are internalized would be highly useful for many targeted therapeutic approaches where internalization is essential (e.g. immunotoxins, targeted liposomes, targeted gene therapy vectors and others).

A) Receptor Mediated Internalization of F5 or C1 Phage

To determine proof of principle of utilized C6.5 phage and C6.5 diabody phage (see, application U.S. Ser. No. 08/665, 202, now U.S. Pat. No. 5,997,322). We have previously shown that C6.5 scFv is internalized, but at a slow rate, and that the C6.5 diabody is somewhat better internalized (probably because it causes receptor dimerization). C6.5 phage, C6.5 diabody phage or an irrelevant anti-Botulinum phage were incubated with SKBR3 cells (ErbB2 expressing breast tumor cell line) at either 37° C. or 4° C. and non-internalized phage removed by sequential washing with PBS and low pH glycine buffer. The cells were then permeabilized and biotinylated anti-M13-antibody added followed by streptavidin Texas Red. Cells were then examined by using a confocal microscope. Both C6.5 phage and C6.5 diabody phage were observed within the cytoplasm. Approximately 1% of cells had internalized C6.5 phage and 20% of the cells had internalized C6.5 diabody phage. There was no internalization of the anti-Botulinum phage.

To determine if infectious phage could be specifically taken up and recovered from within cells, C6.5 phage or C6.5 diabody phage were incubated with SKBR3 cells at 37° C. Non bound phage were removed by washing with PBS and phage bound to the cell surface were eluted by washing twice with low pH glycine. The cells were then lysed and each fraction (the first and second glycine washes and the cytoplasmic fraction) used to infect *E. coli* TG1. Twenty times (C6.5) or 30 times (C6.5 diabody) more phage were bound to the cell surface than the anti-Botulinum phage (glycine 1 wash) (Table 4). After the second glycine wash, the titre of infectious phage from the cell surface decreased, indicating that washing was effective at removing surface bound phage (Table 4). After cell lysis, the titer increased more than 10 fold (C6.5 phage) or 50 fold (C6.5 diabody phage) from the second glycine wash. We believe this titre represents phage recovered from inside the cell. Recovery of phage from inside the cell was 100 times higher for ErbB2 binding C6.5 than for anti-Botulinum phage and 200 fold higher for C6.5 diabody phage (Table 4).

TABLE 4

Titer of cell surface bound phage and internalized phage. $5.0 \times 10^{11}$ phage (anti-Botulinum or anti-ErbB2) were incubated with approximately $1.0 \times 10^5$ ErbB2 expressing SKBR3 cells at 37° C. Cells were washed 10 times with PBS and surface bound phage eluted with two low pH glycine washes. The cells were then washed once with PBS and the cells lysed to release internalized phage. The phage titer was then determined for each of the glycine washes and for the lysed cell fraction by infection of *E. coli* TG1.

| Phage specificity | 1st glycine wash | 2nd glycine wash | Lysed cell fraction |
|---|---|---|---|
| anti-Botulinum | $6.0 \times 10^5$ | $1.0 \times 10^5$ | $6.0 \times 10^5$ |
| Anti-ErbB2 (C6.5 scFv) | $1.2 \times 10^7$ | $5.2 \times 10^6$ | $6.8 \times 10^7$ |
| Anti-ErbB2 (C6.5 diabody) | $1.8 \times 10^7$ | $2.8 \times 10^6$ | $1.7 \times 10^7$ |

Taken together, the results indicate that: 1) phage binding cell surface receptors can be taken up by cells and the infectious phage recovered from the cytoplasm. The amount of uptake is significantly greater than uptake of non-binding phage, and the 100 to 200 fold difference is well within the range that would allow enrichment from a library. What is unknown from the results is whether the phage antibodies are mediating receptor mediated internalization or whether they are merely taken up after binding by membrane turnover.

B) Selection and Characterization of Internalizing Antibodies from a Phage Antibody Library The results described above encouraged us to attempt selection of the phage antibody library described above to identify new phage antibodies that were internalized. Phage antibodies were rescued from the library and selected on SKBR3 cells. For selection, phage were incubated with cells at 37° C., non-binding phage removed by washing cells with PBS and phage bound to cell surface antigens removed by sequential washes with low pH glycine. Cells were then lysed to release internalized phage and the lysate used to infect *E. coli* TG1 to prepare phage for the next round of selection. Three rounds of selection were performed. One hundred clones from each round of selection were analyzed for binding to SKBR3 cells and to ErbB2 extracellular domain by ELISA. We hypothesized that we were likely to obtain binders to ErbB2 since SKBR3 cells are known to express high levels and ErbB2 is a receptor which is known to be internalized. After each round of selection, the titer of phage recovered from the cytoplasm increased (Table 5). After the third round, 45% of the clones were positive SKBR3 cell binding and 17% bound ErbB2 (Table 5).

TABLE 5

Results of selection of a phage antibody library for internalization. For each round of selection, the titer of phage in lysed cells, number of cells lysed and number of phage per cell is indicated. After the third round, individual clones were analyzed for binding to SKBR3 cells by ELISA and to ErbB2 ECD by ELISA.

| Round of selection | # of phage in cell lysate | # of cells lysed | # of phage/cell | % SKBR3 binders | % ErbB2 binders |
|---|---|---|---|---|---|
| 1 | $3.5 \times 10^4$ | $2.8 \times 10^6$ | 0.013 | ND | ND |
| 2 | $1.2 \times 10^5$ | $2.8 \times 10^6$ | 0.038 | ND | ND |
| 3 | $7.5 \times 10^6$ | $2.8 \times 10^6$ | 3.75 | 45% | 17% |

To estimate the number of unique binders, the scFv gene from ELISA positive clones was PCR amplified and fingerprinted by digestion with BstN1. Two unique restriction patterns were identified. The scFv genes were sequenced and 2 unique ErbB2 binding scFv identified. Similar analysis of 5 SKBR3 ELISA positive clones that did not bind ErbB2 identified an additional 11 unique scFv.

To verify that phage antibodies were specific for SKBR3 cells, phage were prepared from each unique clone and analyzed for binding to SKBR3 cells (high ErbB2 expression) as well as 2 other epithelial tumor cell lines (SK-OV-3, moderate ErbB2 expression and MCF7, low ErbB2 expression) and a normal breast cell line (HS578B). Each unique clone specifically stained tumor cell lines but not the normal breast cell line.

SKBR3 and MCF7 cells were incubated with phage antibodies C6.5 (positive control), 3TF5 and 3GH7. The latter two clones were isolated from the library, with 3TF5 binding ErbB2 and the antigen bound by 3GH7 unknown. All 3 phage antibodies intensely stain SKBR3 cells (the selecting cell line and high ErbB2 expresser. C6.5 phage weakly stain MCF7 cells (low ErbB2 expressor). The anti-ErbB2 clone 3TF5 from the library stains MCF7 cells much more intensely then C6.5, as does 3GH7.

SKBR3, SK-OV-3, MCF7 and HST578 cells were studied using native purified scFv 3TF5 and 3GH7. For these studies, the scFv genes were subcloned into a vector which fuses a hexahistidine tag to the scFv C-terminus scFv was then expressed, harvested from the bacterial periplasm and purified by immobilized metal affinity chromatography. The two scFv intensely stain SKBR3 cells, and do not stain the normal breast cell line HST578. There is minimal staining of the low ErbB2 expressing cell line MCF7 and intermediate staining of SK-OV-3 cells (moderate ErbB2 expresser). In general, the intensity of staining is less than seen with phage. This is to be expected since the secondary antibody for phage staining recognizes the major coat protein (2500 copies/phage) resulting in tremendous signal amplification.

The anti-ErbB2 phage antibody 3TF5 was studied further to determine if it was indeed internalized. This antibody was selected for initial study since its internalization could be compared to ErbB2 binding C6.5. $5.0 \times 10^{11}$ 3 TF5 or C6.5 phage were incubated with SKBR3 cells at 37° C. or at 4° C. After washing with PBS, 3TF5 phage stained cells more intensely than C6.5 phage. After washing with low pH glycine, confocal microscopy revealed that 3TF5 phage were internalized by greater than 95% of cells, while C6.5 was internalized by only a few percent of cells. Incubation of either antibody at 4° C. led to no internalization.

The native purified 3TF5 scFv was similarly analyzed and was also efficiently internalized by SKBR3 cells. It should be noted that the native 3TF5 scFv existed only as a monomer with no appreciable dimerization or aggregation as determined by gel filtration.

These experiments demonstrate that phage antibodies can be internalized by cells and recovered from the cytoplasm. Phage that bind an internalizing cell surface receptor can be enriched more than 100 fold over non-binding phage. This level of enrichment is greater than that achieved by selecting on the cell surface. We have applied this approach to library selection and isolated phage antibodies that bind and are internalized by SKBR-3 cells. Several of these antibodies bind to ErbB2, but are more efficiently internalized than antibodies such as C6.5 that were generated by selecting on pure antigen. Many other antibodies have been isolated that bind specifically to SKBR-3 and other breast tumor cell lines and are efficiently internalized. These antibodies should prove useful for tumor targeting and for identifying potentially novel internalizing tumor cell receptors.

Example 3

Increasing the Affinity of Antibody Fragments with the Desired Binding Characteristics by Creating Mutant Phage Antibody Libraries and Selecting on the Appropriate Breast Tumor Cell Line Phage display has the potential to produce antibodies with affinities that cannot be produced using conventional hybridoma technology. Ultra high affinity human antibody fragments could result in excellent tumor penetration, prolonged tumor retention, and rapid clearance from the circulation, leading to high specificity. We therefore undertook a series of experiments to develop methodologies to generate ultra high affinity human antibody fragments. Experiments were performed to answer the following questions: 1) What is the most effective way to select and screen for rare higher affinity phage antibodies amidst a background of lower affinity binders; 2 What is the most effective means to remove bound phage from antigen, to ensure selection of the highest affinity phage antibodies; 3) What is the most efficient techniques for making mutant phage antibody libraries (random mutagenesis or site directed mutagenesis; 4) What region of the antibody molecule should be selected for mutagenesis to most efficiently increase antibody fragment affinity.

To answer these questions, we studied the human scFv C6.5, which binds the extracellular domain (ECD) of the tumor antigen ErbB-2 (32) with a $K_d$ of $1.6 \times 10^{-8}$ M and $k_{off}$ of $6.3 \times 10^{-3}$ s$^{-1}$ (Schier et al. (1995) *Immunotechnology*, 1: 63-71). Isolation and characterization of C6.5 is described briefly below and in detail in application U.S. Ser. No. 08/665, 202, now U.S. Pat. No. 5,997,322.

Despite excellent tumor:normal tissue ratios in vivo, quantitative delivery of C6.5 was not adequate to cure tumors in animals using radioimmunotherapy (Schier et al. (1995) *Immunotechnology*, 1: 63-71). To improve the quantitative delivery of antibody to tumor, the affinity of C6.5 was increased. First, techniques were developed that allowed selection of phage antibodies on the basis of affinity, rather than differential growth in *E. coli* or host strain toxicity (Schier et al. (1996) *J. Mol. Biol.* 255: 28-43; Schier et al. (1996) *Gene* 169: 147-155; Schier et al. (1996) *Human antibodies and hybridomas* 7: 97-105). Next, we determined which locations in the scFv gene to mutate to achieve the greatest increments in affinity (Schier et al. (1996) *J. Mol. Biol.* 255: 28-43; Schier et al. (1996) *Gene*; Schier et al. (1996) *J. Mol. Biol.* 263: 551-567). Random mutagenesis did not yield as great an increment in affinity as site directed mutagenesis of the complementarity determining regions (CDRs) that contain the amino acids which contact antigen. Results from diversifying the CDRs indicated that: 1) the greatest increment in affinity was achieved by mutating the CDRs located in the center of the binding pocket ($V_L$ and $V_H$ CDR3); 2) half of the CDR residues have a structural role in the scFv and when mutated return as wild-type; and 3) these structural residues can be identified prior to library construction by modeling on a homologous atomic crystal structure. These observations led to development of a generic strategy for increasing antibody affinity where mutations are randomly introduced sequentially into $V_H$ and $V_L$ CDR3, with conservation of residues postulated to have a structural role by homology modeling (Schier et al. (1996) *J. Mol. Biol.* 263: 551-567). Using this approach, the affinity of C6.5 was increased 1200 fold to a $K_d$ of $1.3 \times 10^{-11}$ M (Id.).

Biodistribution studies revealed a close correlation between affinity and the percent injected dose of scFv/gram of tumor (% ID/g) at 24 hours (Adams et al. (1998) *Cancer Res.* 58: 485-490). The greatest degree of tumor retention was observed with $^{125}$I-C6ML3-9 (1.42% ID/g, $K_d$=1.0×10$^{-9}$ M). Significantly less tumor retention was achieved with $^{125}$I-C6.5 (0.80% ID/g, $K_d$=1.6×10$^{-8}$) and C6G98A (0.19% ID/g, $K_d$=3.2×10$^{-7}$ M). The tumor:normal organ ratios also reflected the differences in affinity, e.g. tumor:blood ratios of 17.2, 13.3, 3.5 and 2.6, and tumor to liver ratios of 26.2, 19.8, 4.0 and 3.1 for C6ML3-9, C6.5 and C6G98A respectively at 24 hours. Studies of the higher affinity scFv are pending. The results demonstrate our ability to increase antibody affinity to values not achievable from hybridoma technology and confirm the importance of affinity in tumor targeting Example 4

Preclinical Development of C6.5 Based Breast Cancer Therapies

Two approaches have been collaboratively pursued to develop C6.5 based breast cancer therapies. In one collaboration, C6.5 based molecules are being engineered for radioimmunotherapy. To increase quantitative tumor delivery and retention of antibody fragment, dimeric scFv 'diabodies' were created by shortening the linker between the $V_H$ and $V_L$ domains from 15 to 5 amino acids. Consequently, pairing occurs between complementary domains of two different chains, creating a stable noncovalently bound dimer with two binding sites. In vitro, diabodies produced from the V-genes of C6.5 have a significantly higher apparent affinity and longer retention on the surface of SK-OV-3 cells compared to C6.5 scFv ($T_{1/2}$>5 hr vs. 5 min) (Adams et al. (1998) *Brit. J. Cancer.*). Biodistribution studies of C6.5 diabody revealed 6.5% ID/g tumor at 24 hours compared to only 1% ID/g for C6.5 scFv. When diabody retentions were examined over 72 hours and cumulative area under the curve (AUC) values determined, the resulting tumor:organ AUC ratios were greater than reported for other monovalent or divalent scFv molecules. The therapeutic potential of these molecules is being examined in radioimmunotherapy studies in nude mice. Since in vivo characterization of c6.5 based molecules was not formally one of the technical objectives, we are continuing to use the affinity mutants of C6.5 and C6.5 based diabodies to study the relationship between antibody affinity, size and valency and specific tumor targeting as part of NIH R01 1 CA65559-01A1.

In a second collaboration, C6.5 based molecules are being used to target doxorubicin containing stealth liposomes to ErbB2 expressing breast cancers (Kirpotin et al. (1997) *Biochemistry.* 36: 66-75). To facilitate chemical coupling of the scFv to liposomes, the C6.5 gene was subcloned into an *E. coli* expression vector resulting in addition of a free cysteine residue at the C-terminus of the scFv. Purified C6.5cys scFv was conjugated to liposomes and in vitro uptake determined using SKBR3 cells. Total uptake was 3.4 mmol phospholipid/10$^6$ cells at 6 hour, with 70% of the uptake internalized. The uptake is comparable to that achieved using the 4D5 anti-HER2 Fab' from Genentech. There was no uptake of unconjugated liposomes. The results indicate that C6.5 binds to a ErbB2 epitope that results in internalization at a rate comparable to the best internalizing antibody produced from hybridomas (4D5). In vivo therapy studies in scid mice indicated that C6.5 targeted liposomes caused a greater degree of tumor regression and a higher cure rate than untargeted liposomes or a combination of untargeted liposomes and systemic 4D5 antibody.

Conclusions

The experiments described herein establish that A large (7.0×10$^9$ member) phage antibody library has been created which can provide panels of human antibodies to purified antigens with affinities comparable to the affinities of antibodies produced by murine immunization. The phage antibodies binding cell surface receptors can be can be internalized by cells and recovered in an infectious state from within the cell. Methodologies were developed which permit enrichment of internalizing phage antibodies over non-internalizing antibodies more than 100 fold. These methodologies were then applied to select new scFv antibodies that bind to internalizing receptors on SKBR-3 cells. Several of these antibodies bind to ErbB2, but are internalized more efficiently than C6.5 based scFv. Many more antibodies bind to unknown internalizing receptors. All of these scFv bind specifically to SKBR-3 cells or related tumor cell lines. The results indicate that this selection approach is a powerful approach to generate antibodies that can distinguish one cell type (malignant) from another (non-malignant). Moreover, we have demonstrated that it is not only possible to select for binding, but to select for function (internalization). In the near term, we will further characterize the antibodies isolated with respect to specificity, and in the case of ErbB2 binding scFv, affinity. In the longer term we will use these reagents to: 1) study the effect of affinity and valency on the rate of internalization; and 2) identify the antigens bound using immunoprecipitation. It is likely that the results will lead to the identification of novel internalizing tumor cell surface receptors which will be useful therapeutic targets. If this approach proves useful, we plan on applying it to primary tumor cells and DCIS. We also intend to evaluate 3TF5 (ErbB2 binding scFv which is internalized faster than C6.5) for liposome targeting. It is possible that it will be more effective than C6.5

In addition, the experiments demonstrate that methodologies for increasing antibody affinity in vitro to values not previously achieved in vivo. We have applied these methodologies to generate novel ErbB2 binding scFv.

Example 5

Epitope Mapping of F5 and C1

Two unique phage antibodies were identified which were internalized by SKBR-3 cells (F5 and C1 described above). Neither of these phage were isolated when the same library was selected on recombinant ErbB2. To determine why, the $K_d$ of F5 (3.2×10$^{-7}$ M) and C1 ($K_d$=1.0×10$^{-6}$ M) were measured. These $K_d$ are significantly higher than the $K_d$ measured for four of the scFv selected on recombinant ErbB2 ($K_d$=0.1 to 0.65 nM). The higher $K_d$ internalizing phage antibodies would have to compete with the lower $K_d$ non-internalizing phage antibodies for selection on recombinant ErbB2 and were likely lost during the selection process. Since antibodies which are internalized as monomers are likely to be rare, and since there will be many more phage antibodies of lower affinity than higher affinity in a library, it is not surprising that the internalizing antibodies are of high $K_d$. Since antibodies which are internalized are likely to be rare, we hypothesized that it was likely that F5 and C1 recognized the same epitope. This was confirmed using a competition assay (FIG. 2). Thus as hypothesized, F5 and C1 recognize the same epitope, and a different epitope than C6.5. Using the same assay, we confirmed that F5 and C1 recognize a different epitope than the Genentech anti-ErbB2 antibody 4D5 (when humanized known as Herceptin).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A single-chain variable fragment (scFv) antibody, wherein the antibody comprises each of three light chain variable region CDRs and each of three heavy chain variable region CDRs of F5 antibody as encoded by ATCC plasmid deposit designation PTA-7843.

2. The antibody of claim 1, wherein the antibody comprises the F5 antibody as encoded by ATCC plasmid deposit designation PTA-7843.

3. The antibody of claim 1, wherein the antibody is coupled to a liposome.

4. The liposome-coupled antibody of claim 3, wherein the liposome bears an external hydrophilic polymer.

5. The liposome-coupled antibody of claim 4, wherein the external hydrophilic polymer is a polyethylene glycol (PEG).

6. The liposome-coupled antibody of claim 4, wherein the antibody is coupled to the liposome through the external hydrophilic polymer.

7. The liposome-coupled antibody of claim 6, wherein the liposome is a doxorubicin containing liposome.

8. The liposome-coupled antibody of claim 7, wherein the liposome is taken up by SKBR3 cells in vitro.

9. The antibody of claim 1, wherein the antibody comprises a C-terminal cysteine residue.

10. The antibody of claim 9, wherein the antibody comprises the F5 antibody as encoded by ATCC plasmid deposit designation PTA-7843.

11. The antibody of claim 10, wherein the antibody is coupled to a liposome.

12. The liposome-coupled antibody of claim 11, wherein the liposome bears an external hydrophilic polymer.

13. The liposome-coupled antibody of claim 12, wherein the external hydrophilic polymer is a polyethylene glycol (PEG).

14. The liposome-coupled antibody of claim 12, wherein the antibody is coupled to the liposome through the external hydrophilic polymer.

15. The liposome-coupled antibody of claim 14, wherein the antibody is coupled to the liposome through the polyethylene glycol.

16. The liposome-coupled antibody of claim 15, wherein the liposome is a doxorubicin containing liposome.

17. The liposome-coupled antibody of claim 16, wherein the liposome is taken up by SKBR3 cells in vitro.

18. A pharmaceutical composition comprising the liposome-coupled antibody of claim 16 in a pharmaceutically acceptable carrier.

19. A method of treating a HER2 positive carcinoma, the method comprising administering the composition of claim 18 to a patient suffering from a HER2 positive carcinoma in therapeutically effective dose.

20. The method of claim 19, wherein the composition is administered by single or multiple administrations.

21. The method of claim 19, wherein the composition is administered intravenously.

* * * * *